United States Patent
Konno et al.

(10) Patent No.: US 10,145,816 B2
(45) Date of Patent: Dec. 4, 2018

(54) GAS SENSOR ELEMENT, GAS SENSOR, AND METHOD OF MANUFACTURING GAS SENSOR ELEMENT

(71) Applicant: NGK SPARK PLUG CO., LTD., Nagoya-shi, Aichi (JP)

(72) Inventors: Takashi Konno, Komaki (JP); Satoshi Okazaki, Kasugai (JP); Masaki Nakagawa, Komaki (JP); Haruhiko Shigeta, Iwakura (JP)

(73) Assignee: NGK SPARK PLUG CO., LTD., Nagoya-shi, Aichi (JP)

( * ) Notice: Subject to any disclaimer, the term of this patent is extended or adjusted under 35 U.S.C. 154(b) by 235 days.

(21) Appl. No.: 14/863,509

(22) Filed: Sep. 24, 2015

(65) Prior Publication Data
US 2016/0091457 A1 Mar. 31, 2016

(30) Foreign Application Priority Data
Sep. 25, 2014 (JP) .................... 2014-195496

(51) Int. Cl.
*G01N 27/407* (2006.01)

(52) U.S. Cl.
CPC ..... *G01N 27/4071* (2013.01); *G01N 27/4073* (2013.01)

(58) Field of Classification Search
CPC ........... G01N 27/4073; G01N 33/0009; G01N 27/4074; G01N 27/4075; G01N 27/4077; G01N 27/4067; G01N 27/4071; G01N 27/409; G01N 27/407; G01N 33/0027; G01N 33/0036
See application file for complete search history.

(56) References Cited

U.S. PATENT DOCUMENTS

2013/0075256 A1* 3/2013 Saitou ................ H01G 9/0036
204/427

FOREIGN PATENT DOCUMENTS

| JP | 2007-278941 | A | | 10/2007 |
| JP | 2007278941 | A | * | 10/2007 |
| JP | 5104744 | B2 | | 12/2012 |

OTHER PUBLICATIONS

Machine translation of JP 2007-278941, Mori et al.*

* cited by examiner

*Primary Examiner* — Mayla Gonzalez Ramos
(74) *Attorney, Agent, or Firm* — Sughrue Mion, PLLC

(57) ABSTRACT

A gas sensor element (10) includes a composite ceramic layer (111) having an insulation portion (112) and an electrolyte portion (131) disposed within a through hole (112*h*), and a first conductor layer (150) extending in a continuous manner on a first insulation main surface (113) as well as on a first electrolyte main surface (133). The electrolyte portion (131) is thinner than the insulation portion (112), and the first electrolyte main surface (133) is located on a thickness-direction inward side DTN. The insulation portion (112) has, on a first insulation main surface side, a protruding portion (122) overlying the first electrolyte main surface (133). The thickness of the protruding portion (122) reduces toward the inward side DR1 of the through hole (112*h*). The first conductor layer (150) extends in a continuous manner on a protrusion surface (122*s*) as well as on the first electrolyte main surface (133).

10 Claims, 21 Drawing Sheets

GAS SENSOR ELEMENT, GAS SENSOR, AND METHOD OF MANUFACTURING GAS SENSOR ELEMENT

TECHNICAL FIELD

The present invention relates to a gas sensor element for detecting gas to be measured, a gas sensor having the gas sensor element, and a method of manufacturing the gas sensor element.

BACKGROUND ART

Patent Document 1, for example, discloses a gas sensor element having a composite layer in which a solid electrolyte body (electrolyte portion to be described herein later) and an insulation member (insulation portion to be described herein later) exist. In Patent Document 1, the dimensional difference between the thickness of the solid electrolyte body and the thickness of the insulation member is rendered equal to or less than the thickness of an electrode (conductor layer). Thus, a portion of the electrode laminated on the solid electrolyte body and a portion laminated on the insulation member are at least partially in contact with each other, whereby breaking of the electrode at a portion on the boundary between the solid electrolyte body and the insulation member can be prevented.

PRIOR ART DOCUMENT

Patent Document

[Patent Document 1] Japanese Patent Application Laid-Open (kokai) No. 2007-278941

SUMMARY OF THE INVENTION

Problem to be Solved by the Invention

However, in the gas sensor element of Patent Document 1, since a step-like level difference exists at the boundary between the solid electrolyte body (electrolyte portion) and the insulation member (insulation portion), the electrode (conductor layer) extending in a continuous manner on the solid electrolyte body (electrolyte portion) as well as on the insulation member (insulation portion) is apt to crack or break at a portion on the boundary.

The present invention has been conceived in view of the above problem and provides a gas sensor element which includes a composite ceramic layer having an electrolyte portion and an insulation portion, and a conductor layer extending in a continuous manner on the electrolyte portion as well as on the insulation portion and is, yet, unlikely to suffer cracking or breaking of the conductor layer at a portion on the boundary between the electrolyte portion and the insulation portion to thereby provide high reliability, as well as a gas sensor having the gas sensor element. The present invention also provides a method of manufacturing the gas sensor element.

Means for Solving the Problem

A mode of the present invention provides a gas sensor element comprising a composite ceramic layer having a plate-like insulation portion formed of an insulating ceramic and having a through hole extending therethrough in a thickness direction and a plate-like electrolyte portion formed of a solid electrolyte ceramic and disposed within the through hole, and a first conductor layer extending in a continuous manner on a first insulation main surface of the insulation portion intersecting with the thickness direction as well as on a first electrolyte main surface of the electrolyte portion intersecting with the thickness direction, wherein the electrolyte portion has a thickness smaller than that of the insulation portion; the first electrolyte main surface of the electrolyte portion is located on a thickness-direction inward side with respect to the first insulation main surface of the insulation portion; the insulation portion has, on a first insulation main surface side, a protruding portion overlying the first electrolyte main surface of the electrolyte portion and protruding toward an inward side of the through hole; the protruding portion has a form in which its thickness reduces toward the inward side of the through hole and in which a protrusion surface of the protruding portion located on a thickness-direction outward side extends toward the inward side of the through hole as well as toward the thickness-direction inward side; and the first conductor layer extends in a continuous manner on the protrusion surface as well as on the first electrolyte main surface.

In the composite ceramic layer of the above-mentioned gas sensor element, the first electrolyte main surface of the electrolyte portion is located on the thickness-direction inward side with respect to the first insulation main surface of the insulation portion. Furthermore, the insulation portion has, on the first insulation main surface side, the protruding portion which overlies the first electrolyte main surface of the electrolyte portion, whose thickness reduces toward the inward side of the through hole, and whose protrusion surface extends toward the inward side of the through hole as well as toward the thickness-direction inward side. That is, the level difference between the first insulation main surface of the insulation portion and the first electrolyte main surface of the electrolyte portion is mitigated at the protruding portion.

Therefore, the first conductor layer extending between a region on the protruding portion of the first insulation main surface and a region on the first electrolyte main surface is unlikely to suffer cracking or breaking at a portion on the boundary between the region on the protruding portion of the first insulation main surface and the region on the first electrolyte main surface, whereby the gas sensor element provides high reliability.

The gas sensor element comprises the composite ceramic layer and the first conductor layer. The gas sensor element may include that in the form of a laminate of the composite ceramic layer, another insulating ceramic layer, a spacer-use insulating ceramic layer having a through hole, a cutout, or a groove formed therein for forming a space within the element, another composite ceramic layer, a conductor layer, etc.

Also, the gas sensor element has not only a form in which the second conductor layer is formed on the second electrolyte layer main surface of the electrolyte portion located opposite the first electrolyte main surface and adapted to form a cell element or a pump element in cooperation with the first conductor layer through the electrolyte portion but also a form in which the second conductor layer is formed on the first electrolyte main surface; i.e., the first conductor layer and the second conductor layer are formed on the first electrolyte main surface.

Furthermore, the composite ceramic layer may have a form in which the second electrolyte main surface of the electrolyte portion is located on a thickness-direction outward side with respect to the second insulation main surface of the insulation portion; i.e., the second electrolyte main surface protrudes from the second insulation main surface. Also, the composite ceramic layer may have a form in which the second electrolyte main surface is located on the thickness-direction inward side with respect to the second insulation main surface of the insulation portion located opposite the first insulation main surface; i.e., the second electrolyte main surface is depressed with respect to the second insulation main surface; however, preferably, the composite ceramic layer has a form in which, as mentioned below, the second electrolyte main surface of the electrolyte portion and the second insulation main surface of the insulation portion are flush with each other.

The protruding portion of the insulation portion may be formed along the entire perimeter of the through hole or along only a portion of the perimeter of the through hole.

According to an example form of the first conductor layer, the first conductor layer includes a first electrode layer formed on the first electrolyte main surface and a first extension layer extending from the first electrode layer onto the first insulation main surface. Preferably, the entire perimetric edge of the first electrode layer is depressed into the through hole with respect to the inner perimetric edge of the first insulation main surface (including the protrusion surface) of the insulation portion. Also, a portion or the entirety of the perimetric edge of the first electrode layer may reach the inner perimetric edge of the first insulation main surface. According to an example form of the first extension layer, the first extension layer extends from a portion of the outer perimetric edge of the first electrode layer toward the outward side of the through hole on the first insulation main surface, as in the case of a strip-like lead layer whose width is smaller than that of the first electrode layer. According to another form of the first extension layer, the first extension layer extends onto the first insulation main surface along the entire perimeter of the first electrode layer; i.e., the conductor layer extends from the entire perimetric edge of the first electrode layer toward the outward side of the through hole on the first insulation main surface and surrounds the first electrode layer.

Preferably, the above-mentioned gas sensor element has a form in which an overlying surface of the first electrolyte main surface which the protruding portion overlies from the thickness-direction outward side has such a form as to extend toward the outward side of the through hole as well as toward the thickness-direction inward side.

This gas sensor element has a form in which the overlying surface of the first electrolyte main surface of the electrolyte portion extends toward the outward side of the through hole as well as toward the thickness-direction inward side; i.e., a form in which the overlying surface approaches the second electrolyte main surface as it progresses toward the outward side of the through hole. Thus, there can be restrained the occurrence of cracking in the protruding portion starting from any portion of the overlying surface.

Notably, a form in which the overlying surface extends toward the outward side of the through hole as well as toward the thickness-direction inward side; i.e., a form in which the overlying surface approaches the second electrolyte main surface as it progresses toward the outward side of the through hole is, for example, a form in which the section of the overlying surface has an arc shape convexed obliquely toward the outward side of the through hole as well as toward the thickness-direction outward side. This form includes a form in which the section of the overlying surface has an outwardly convex arc shape which partially includes a straight line segment and a form in which the section of the overlying surface has an entirely straight shape.

Furthermore, preferably, the above-mentioned gas sensor element is such that the electrolyte portion is formed by firing an electrolyte green sheet which contains the solid electrolyte ceramic.

The thickness of the electrolyte portion has a great effect on properties of an element, such as a cell element or a pump element, composed of the electrolyte portion, the first conductor layer, etc. By contrast, in the above-mentioned gas sensor element, since the electrolyte portion is formed by firing an electrolyte green sheet (specifically, a green electrolyte portion formed of the electrolyte green sheet), which allows easy control of thickness in the course of manufacturing the sheet (before firing) and after firing, the thickness of the electrolyte portion can be rendered uniform among products; thus, properties of an oxygen concentration cell composed of the electrolyte portion and the first electrode layer can be rendered uniform among the gas sensor elements.

Furthermore, since the electrolyte portion is thinner than the insulation portion, although pressure is applied in the thickness direction to a green composite ceramic layer for lamination in the course of manufacture, pressure is unlikely to be applied to a green electrolyte portion which is to become the electrolyte portion; thus, variation is unlikely to arise in the thickness of the electrolyte portion, which would otherwise result from compression. Therefore, variations in properties can be reduced among the gas sensor elements.

Furthermore, preferably, any one of the above-mentioned gas sensor elements further comprises a second conductor layer extending in a continuous manner on a second insulation main surface of the insulation portion located opposite the first insulation main surface as well as on a second electrolyte main surface of the electrolyte portion located opposite the first electrolyte main surface, wherein the second insulation main surface and the second electrolyte main surface are flush with each other.

In the above-mentioned gas sensor element, the second electrolyte main surface of the electrolyte portion and the second insulation main surface of the insulation portion are flush with each other. Thus, the second conductor layer extending in a continuous manner on the second electrolyte main surface as well as on the second insulation surface is unlikely to suffer cracking or breaking at a portion on the boundary between the second electrolyte main surface and the second insulation main surface, whereby the gas sensor element provides high reliability.

Notably, no particular limitation is imposed on the second conductor layer so long as a portion thereof is formed on the second electrolyte main surface; however, preferably, the second conductor layer is disposed in such a manner as to face a portion of the first conductor layer through the electrolyte portion. By means of a portion (the aforementioned first electrode portion) of the first conductor layer and a portion (a second electrode portion, which will be mentioned below) of the second conductor layer facing each other at a small electrode-to-electrode distance with a large electrode area while the electrode portion formed of a solid electrolyte ceramic intervenes therebetween, an element having good properties, such as a cell element like an oxygen concentration cell, or a pump element adapted to perform oxygen pumping, can be formed.

Also, the second conductor layer extends in a continuous manner on the second electrolyte main surface as well as on the second insulation main surface. The second conductor layer may extend along the entire perimeter of the through hole or along only a portion of the perimeter. According to an example form of the second conductor layer, the second conductor layer includes a second electrode layer formed on the second electrolyte main surface and a second extension layer extending from the second electrode layer onto the second insulation main surface. The second electrode layer may be such that the entire perimetric edge thereof is depressed into the through hole with respect to the outer perimetric edge of the second electrolyte main surface of the electrolyte portion or such that a portion or the entirety of the perimetric edge thereof reaches the outer perimetric edge of the second electrolyte main surface (second insulation main surface of the insulation portion). According to an example form of the second extension layer, the second extension layer extends from a portion of the perimetric edge of the second electrode layer toward the outward side of the through hole onto the second insulation main surface, as in the case of a strip-like lead layer whose width is smaller than that of the second electrode layer. According to another form of the second extension layer, the second extension layer extends onto the second insulation main surface along the entire perimeter of the second electrode layer; i.e., the second extension layer extends from the entire perimetric edge of the second electrode layer toward the outward side of the through hole on the second insulation main surface and surrounds the second electrode layer.

Furthermore, preferably, the above-mentioned gas sensor element is configured such that: the first conductor layer includes a first electrode layer formed on the first electrolyte main surface; the second conductor layer includes a second electrode layer formed on the second electrolyte main surface; the second conductor layer is formed by screen-printing electrode paste, followed by firing; and the above-mentioned gas sensor element is such that, during use, reference gas is in contact with the first electrode layer, whereas gas to be measured is in contact with the second electrode layer.

According to a recent finding, in a gas sensor element in which two electrode layers and the electrolyte portion intervening the electrode layers constitute an oxygen concentration cell with gas to be measured being in contact with one of the electrode layers and reference gas being in contact with the other electrode layer, the thickness of the electrode layer (one of the electrode layers) in contact with gas to be measured has a great effect on properties of the element as compared with the thickness of the electrode layer (the other electrode layer) in contact with reference gas.

In the above-mentioned gas sensor element, the first electrode layer is formed on the first electrolyte main surface which is located on the thickness-direction inward side with respect to the first insulation main surface. Thus, in the case where the first electrode layer is formed by screen-printing electrode paste on the first electrolyte main surface of a green electrolyte portion or a fired electrolyte portion, followed by firing, since screen printing is performed on the first electrolyte main surface depressed from the surrounding first insulation main surface, difficulty is encountered in controlling the thickness of the first electrode layer; as a result, the thickness is apt to vary among products.

Meanwhile, the second electrode layer of the above-mentioned gas sensor element is formed on the second electrolyte main surface which is disposed flush with the second insulation main surface. Thus, in screen printing, the thickness of electrode paste on the second electrolyte main surface, together with the thickness of electrode paste on the second insulation main surface, can be readily controlled. Therefore, the thickness of the second electrode layer after firing can be appropriately controlled. Thus, properties of the oxygen concentration cell can be rendered uniform among the above-mentioned gas sensor elements in which reference gas is in contact with the first electrode layer, whereas gas to be measured is in contact with the second electrode layer formed by screen printing.

Examples of such a gas sensor element include a gas sensor element having one oxygen concentration cell, a gas sensor element having two oxygen concentration cells; i.e., a sensor cell and a pump cell, and a gas sensor element having three oxygen concentration cells (two sensor cells and one pump cell). Examples of such a second electrode layer include one formed by screen-printing electrode paste on the electrode portion of a green composite ceramic layer, followed by firing (cofiring), and one formed by firing electrode paste on the electrolyte portion of a fired composite ceramic layer (postfiring).

Reference gas is, for example, oxygen gas contained in a reference chamber or ambient atmosphere (the atmosphere) in the case of use of an oxygen ion conductive solid electrolyte ceramic (e.g., zirconia).

Preferably, the above-described two sensor elements comprise an ambient-atmosphere introduction path formation member which defines an ambient-atmosphere introduction path for introducing ambient atmosphere to the first electrode layer, and a gas introduction path formation member which defines a gas introduction path for introducing gas to be measured to the second electrode layer.

In the above-mentioned gas sensor element, gas to be measured which is introduced through the gas introduction path comes into contact with the second electrode layer, whereas ambient atmosphere introduced through the ambient-atmosphere introduction path comes into contact with the first electrode layer. Thus, the first electrode layer, the second electrode layer, and the electrolyte portion constitute an oxygen concentration cell, and an electromotive force is generated between the first electrode layer and the second electrode layer in response to the oxygen concentration difference between gas to be measured in contact with the second electrode layer and the atmosphere in contact with the first electrode layer. Therefore, an output from the oxygen concentration cell element can be utilized for detecting the existence of oxygen in or the concentration of oxygen contained in gas to be measured, or detecting the concentration of oxygen-containing gas which contains oxygen atoms, such as $NO_x$ or CO.

The gas introduction path is a gas flow path for introducing gas to be measured to the second electrode layer within the gas sensor element. Specific examples of the gas introduction path are a gas introduction path in the form of a hollow gas flow path, a gas introduction path in the form of a gas flow path locally clogged with a gas-permeable porous body, and a gas introduction path formed entirely of a gas-permeable porous body. Examples of a gas introduction path formation member include a wall member such as an airtight (dense) insulating ceramic layer which forms a hollow gas introduction path (gas flow path) by itself or in cooperation with the composite ceramic layer, and a porous member which is formed of a gas-permeable porous ceramic body and partially or entirely clogs a gas flow path.

The ambient-atmosphere introduction path is a gas flow path for introducing ambient atmosphere (the atmosphere) to the first electrode layer within the gas sensor element. Specific examples of the ambient-atmosphere introduction path are an ambient-atmosphere introduction path in the form of a hollow gas flow path, and an ambient-atmosphere introduction path in the form of a gas flow path which is partially or entirely clogged with an ambient-atmosphere-permeable porous metal or ceramic body, such as a gas flow path-curr-first extension layer formed of an ambient-atmosphere permeable porous metal body and serving also as the first extension layer connected to the first electrode layer. Examples of an ambient-atmosphere introduction path formation member include a wall member such as an airtight (dense) insulating ceramic layer which forms a hollow ambient-atmosphere introduction path (gas flow path) by itself or in cooperation with the composite ceramic layer, and a porous member, such as an ambient-atmosphere-permeable porous metal member or an ambient-atmosphere-permeable porous ceramic member, which partially or entirely clogs the gas flow path.

Furthermore, another mode of the present invention provides a gas sensor comprising any one of the above-mentioned gas sensor elements.

Because of employment of the aforementioned gas sensor element, the above-mentioned gas sensor is unlikely to suffer the occurrence of cracking or breaking of the first conductor layer at a position between the first insulation main surface and the first electrolyte main surface and thus can provide high reliability.

Furthermore, a further mode of the present invention provides a method of manufacturing a gas sensor element which comprises a composite ceramic layer having a plate-like insulation portion formed of an insulating ceramic and having a through hole extending therethrough in a thickness direction, and a plate-like electrolyte portion formed of a solid electrolyte ceramic and disposed within the through hole, and a first conductor layer extending in a continuous manner on a first insulation main surface of the insulation portion intersecting with the thickness direction as well as on a first electrolyte main surface of the electrolyte portion intersecting with the thickness direction, wherein the electrolyte portion has a thickness smaller than that of the insulation portion; the first electrolyte main surface of the electrolyte portion is located on a thickness-direction inward side with respect to the first insulation main surface of the insulation portion; the insulation portion has, on a first insulation main surface side, a protruding portion overlying the first electrolyte main surface of the electrolyte portion and protruding toward an inward side of the through hole; the protruding portion has a form in which its thickness reduces toward the inward side of the through hole and in which a protrusion surface of the protruding portion located on a thickness-direction outward side extends toward the inward side of the through hole as well as toward the thickness-direction inward side; and the first conductor layer extends in a continuous manner on the protrusion surface as well as on the first electrolyte main surface, the method comprising an inserting step of inserting a plate-like green electrolyte portion formed of the solid electrolyte ceramic and being thinner than a plate-like green insulation portion containing the insulating ceramic and having a sheet through hole extending therethrough in a sheet thickness direction, into the sheet through hole in such a manner that the first electrolyte sheet main surface is located on a sheet thickness-direction inward side with respect to a first insulation sheet main surface of the green insulation portion; a compressing step of pressing the first insulation sheet main surface of the green insulation portion to compress the green insulation portion in the sheet thickness direction; a first printing step of forming a green first conductor layer which extends in a continuous manner on the first insulation sheet main surface of the green insulation portion as well as on the first electrolyte sheet main surface of the green electrolyte portion; and a firing step of firing the green insulation portion, the green electrolyte portion, and the green first conductor layer to form the composite ceramic layer having the insulation portion and the electrolyte portion, and the first conductor layer; wherein the compressing step forms a green protruding portion at a first insulation sheet main surface side of the green insulation portion in such a manner as to overlie the first electrolyte sheet main surface of the green electrolyte portion, to protrude toward an inward side of the sheet through hole, and to reduce in thickness toward the inward side.

According to the above-mentioned method of manufacturing a gas sensor element, in the compressing step, the first insulation sheet main surface is pressed to compress the green insulation portion in the sheet thickness direction. By carrying out this procedure, the sheet through hole reduces in size, whereby a sheet through-hole inner perimetric surface which defines the sheet through hole can be brought in close contact with an electrolyte sheet outer perimetric surface of the green electrolyte portion inserted in the sheet through hole.

Also, by means of the green protruding portion being formed by the compressing step, the composite ceramic layer after firing can readily have the protruding portion.

By virtue of formation of the protruding portion, there can be manufactured a highly reliable gas sensor element in which the first conductor layer is unlikely to suffer cracking or breaking at a portion on the boundary between the first electrolyte main surface and the first insulation main surface.

Furthermore, preferably, in the method of manufacturing a gas sensor element, the gas sensor element is such that an overlying surface of the first electrolyte main surface which the protruding portion overlies from the thickness-direction outward side has such a form as to extend toward the outward side of the through hole as well as toward the thickness-direction inward side, and the compressing step forms a green overlying surface of the first electrolyte sheet main surface which the green protruding portion overlies from a sheet thickness-direction outward side, into such a form as to extend toward the outward side of the sheet through hole as well as toward a sheet thickness-direction inward side.

According to this manufacturing method, the compressing step forms the green overlying surface of the first electrolyte sheet main surface of the green electrolyte portion into such a form as to extend toward the outward side of the sheet through hole as well as toward the sheet thickness-direction inward side. Thus, in the composite ceramic layer after firing, there can be appropriately restrained the occurrence of cracking in the protruding portion starting from any portion of the overlying surface.

Furthermore, preferably, in the above-mentioned method of manufacturing a gas sensor element, the gas sensor element further comprises a second conductor layer extending in a continuous manner on a second insulation main surface of the insulation portion located opposite the first insulation main surface as well as on a second electrolyte main surface of the electrolyte portion located opposite the first electrolyte main surface; the second insulation main surface and the second electrolyte main surface are flush with each other; the inserting step inserts the green electrolyte portion in such a manner that a side of the green electrolyte portion corresponding to a second insulation sheet main surface located opposite the first insulation sheet main surface protrudes from the sheet through hole of the green insulation portion; and the compressing step performs compression in such a manner that the second insulation sheet main surface of the green insulation portion and a second electrolyte sheet main surface of the green electrolyte portion located opposite the first electrolyte sheet main surface become flush with each other; the method further comprising a second printing step of forming, by screen printing prior to the firing step, a green second conductor layer which extends in a continuous manner on the second insulation sheet main surface of the green insulation portion as well as on the second electrolyte sheet main surface of the green electrolyte portion.

The inserting step inserts the green electrolyte portion into the sheet through hole in such a manner that the green electrolyte portion protrudes outward from the second insulation sheet main surface of the green insulation portion. Thus, in the compressing step, the protruding green electrolyte portion is pressed into the sheet through hole, whereby the second electrolyte sheet main surface of the green electrolyte portion and the second insulation sheet main surface of the green insulation portion can be readily rendered flush with each other. Thus, there can be easily formed the gas sensor element having the composite ceramic layer in which the second electrolyte main surface of the electrolyte portion is flush with the second insulation main surface of the insulation portion.

By virtue of this, the second conductor layer extending in a continuous manner on the second insulation main surface as well as on the second electrolyte main surface is also unlikely to suffer the occurrence of cracking or breaking at a portion on the boundary between the two main surfaces, so that a gas sensor element having higher reliability can be manufactured.

Furthermore, since the second electrolyte sheet main surface is flush with the second insulation sheet main surface, the thickness of the green second conductor layer formed by screen printing, and, in turn, the thickness of the second conductor layer (particularly, the thickness of the second electrode layer) after firing can be easily controlled.

Notably, a form in which the green electrolyte portion protrudes from the sheet through hole beyond the second insulation sheet main surface of the green insulation portion is, in other words, a form in which the second electrolyte sheet main surface of the green electrolyte portion is located on the sheet thickness-direction outward side with respect to the second insulation sheet main surface of the green insulation portion.

MODES FOR CARRYING OUT THE INVENTION (Embodiment)

Figure 1:
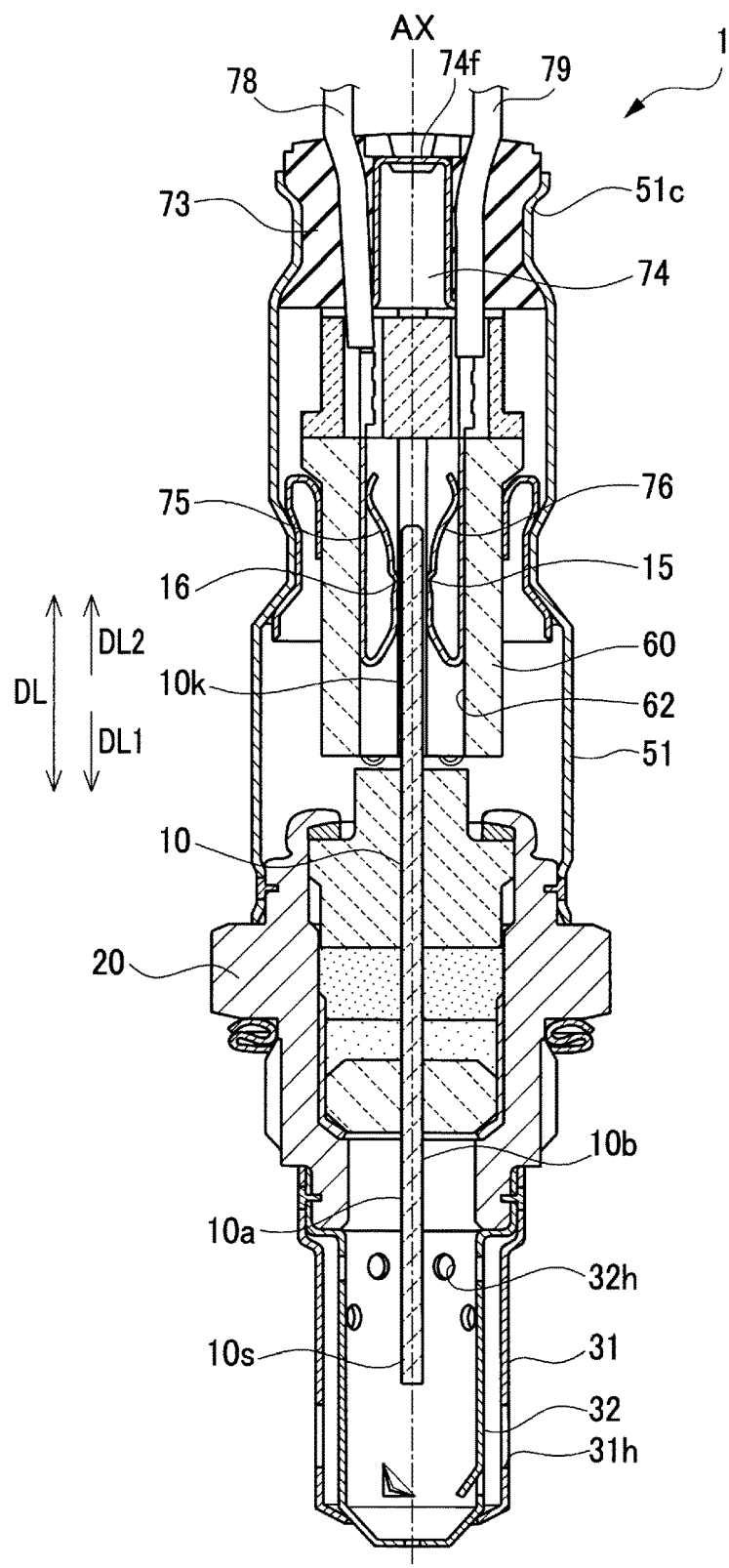
FIG. 1 is a longitudinal sectional view of a gas sensor according to an embodiment.
Figure 2:
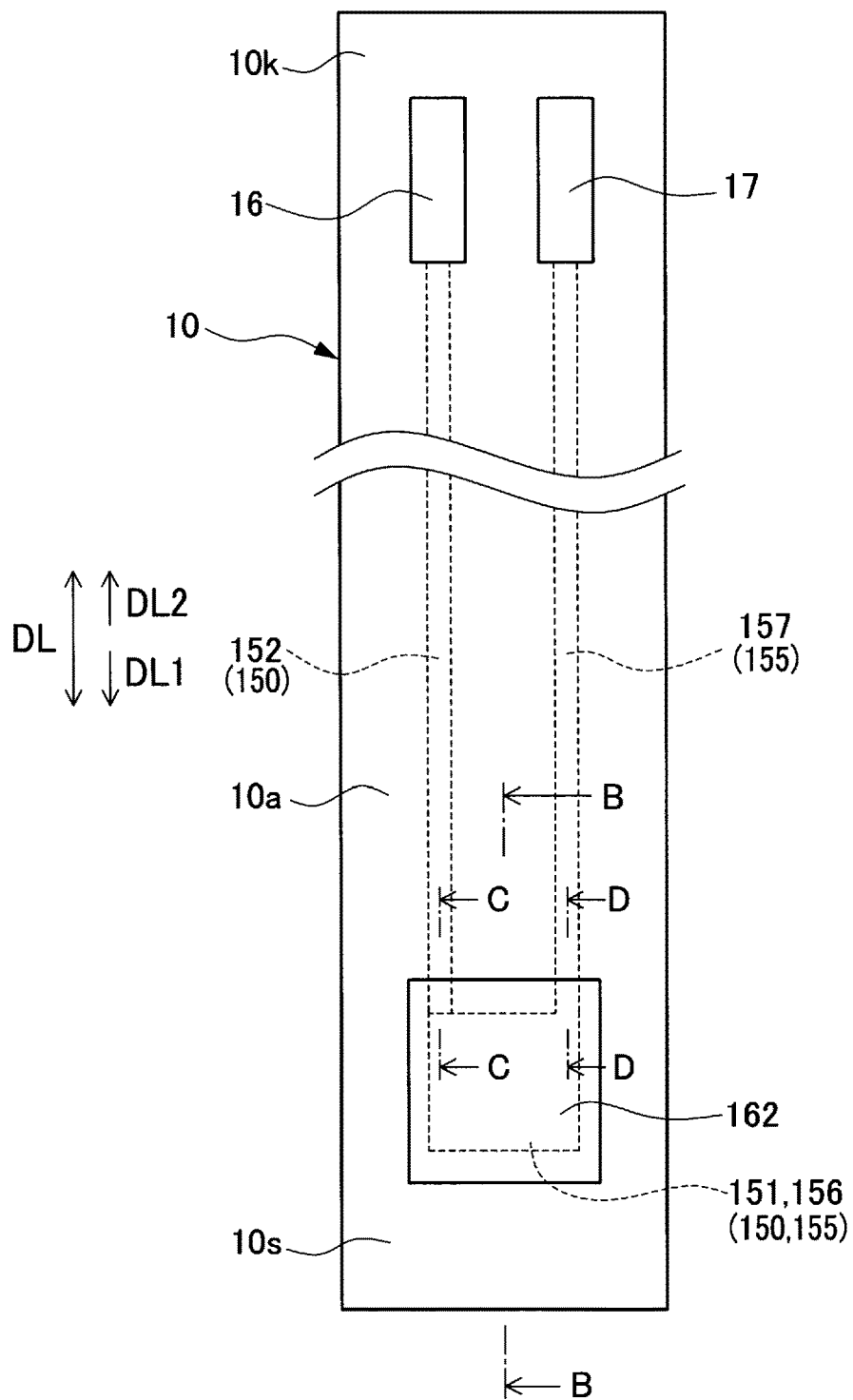
FIG. 2 is a plan view of a gas sensor element according to the embodiment.
Figure 3:
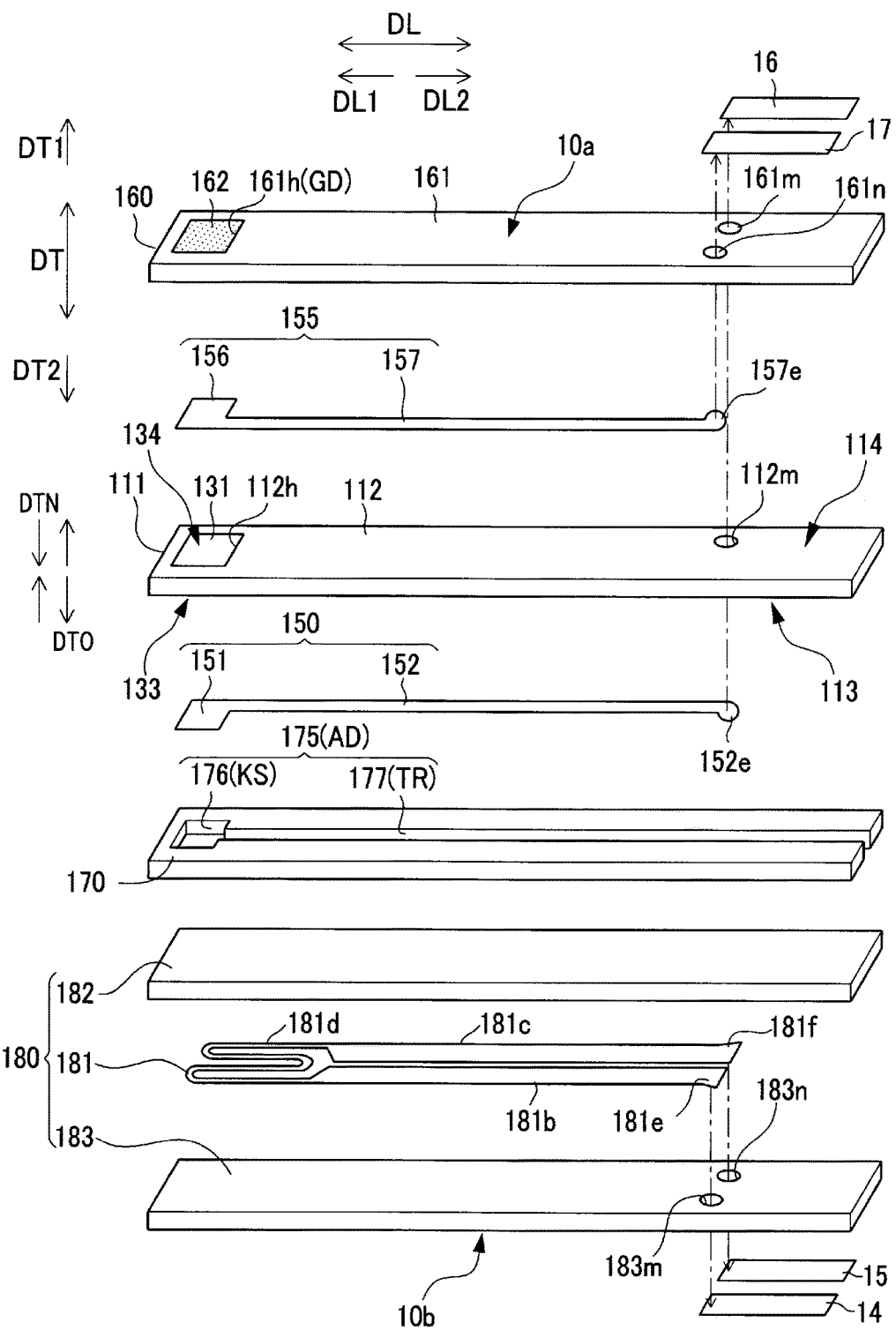
FIG. 3 is an exploded perspective view of the gas sensor element according to the embodiment.
Figure 4:
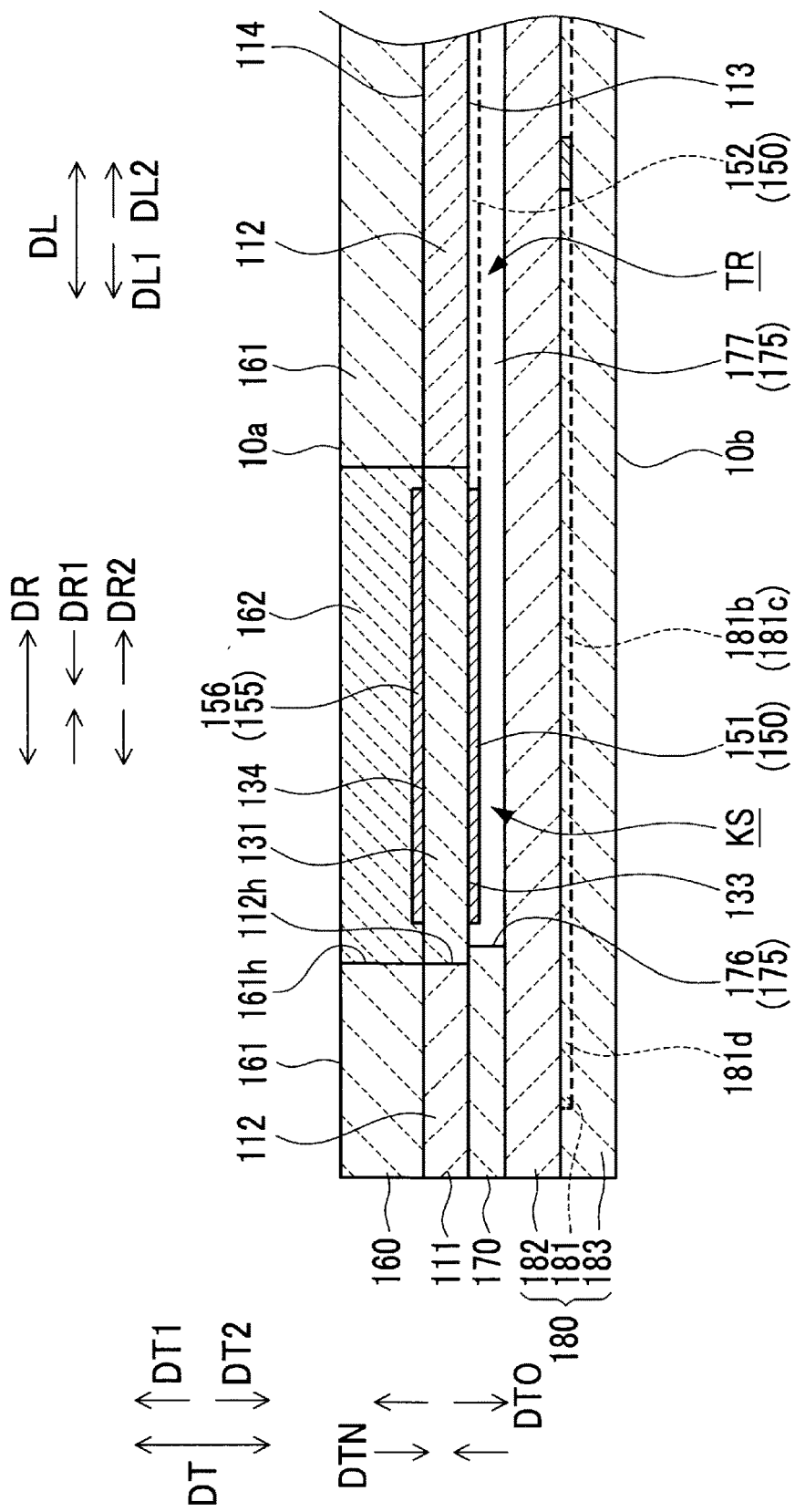
FIG. 4 is an enlarged sectional view (sectional view taken along line B-B of FIG. 2) of the gas sensor element according to the embodiment.

First, a gas sensor 1 having a gas sensor element 10 according to the present embodiment will be described. FIG. 1 is a longitudinal sectional view of the gas sensor 1 according to the embodiment taken along an axial line AX. FIG. 2 is a plan view of the gas sensor element 10 according to the embodiment. FIG. 3 is an exploded perspective view of the gas sensor element 10. FIG. 4 is a sectional view taken along line B-B of FIG. 2.

The gas sensor 1 is an oxygen sensor (see FIG. 1) attached for use to an exhaust pipe (not shown) of an internal combustion engine. The gas sensor 1 includes the gas sensor element 10 capable of detecting the oxygen concentration of exhaust gas, which is gas to be measured, and a tubular metallic shell 20 for holding therein the gas sensor element 10. An outer protector 31 and an inner protector 32 are disposed on the forward side (lower side in FIG. 1) of the metallic shell 20, and an outer tube 51 is disposed on the rear side (upper side in FIG. 1). The gas sensor 1 further includes a separator 60 which is disposed within the outer tube 51 and perimetrically surrounds the gas sensor element 10 and which holds four terminal members 75, 75, 76, and 76 attached to distal ends of four leads 78, 78, 79, and 79, respectively, in such a manner that the terminal members are separated from one another (see FIG. 1).

The metallic shell 20 holds the gas sensor element 10 in such a manner that a forward end portion 10s of the gas sensor element 10 protrudes therefrom forward (downward in FIG. 1) and that a rear end portion 10k of the gas sensor element 10 protrudes therefrom rearward (upward in FIG. 1). The outer protector 31 and the inner protector 32 made of metal cover the forward end portion 10s of the gas sensor element 10. The outer protector 31 and the inner protector 32 have a plurality of holes 31h and 32h, respectively, and gas to be measured can be introduced from outside the outer protector 31 into a surrounding space around the forward end portion 10s of the gas sensor element 10 disposed inside the inner protector 32.

The separator 60 has an insertion hole 62 extending therethrough along the axial line AX (see FIG. 1). The rear end portion 10k of the gas sensor element 10 is inserted into the insertion hole 62. The four terminal members, 75, 75, 76, and 76 are disposed within the insertion hole 62 in such a manner as to be separated from one another and are elastically in contact with pads 14 to 17, which will be described herein later, of the gas sensor element 10 to thereby be electrically connected thereto.

In the gas sensor 1 of the present embodiment, a metal pipe 74 covered with a water-repellent gas-permeable filter 74f is fitted into a grommet 73 plugged into a rear end opening 51c at the rear end (upper end in FIG. 1) of the outer tube 51. Thus, the gas sensor 1 can introduce the atmosphere existing therearound into the outer tube 51 through the filter 74f and, as will be described herein later, up to a surrounding space around the rear end portion 10k of the gas sensor element 10.

The gas sensor element 10 assumes a rectangular plate-like form elongated in a longitudinal direction DL (vertical direction in FIGS. 1 and 2). The gas sensor element 10 is disposed within the gas sensor 1 with its center line coinciding with the axial line AX (see FIG. 1). The gas sensor element 10 has two heater pads 14 and 15 formed on a second element main surface 10b facing the other side DT2 (far side of paper on which FIG. 2 appears; lower side in FIG. 3) with respect to the thickness direction DT at the rear end portion 10k. Also, the gas sensor element 10 has two sensor pads 16 and 17 on a first element main surface 10a facing thickness-direction one side DT1 (upper side in FIGS. 3 and 4) at the rear end portion 10k. The heater pads 14 and 15 are electrically connected to a heater pattern 181, which will be described herein later, within the gas sensor element 10. Also, the sensor pad 16 is electrically connected to a first conductor layer 150 (a first extension layer 152 and a first electrode layer 151) within the gas sensor element 10, and the sensor pad 17 is electrically connected to a second conductor layer 155 (a second extension layer 157 and a second electrode layer 156) within the gas sensor element 10.

The gas sensor element 10 is composed of a plurality of ceramic layers and conductor layers laminated together in the thickness direction DT. Specifically, as shown in FIGS. 3 and 4, in addition to a composite ceramic layer 111 including an insulation portion 112 and an electrolyte portion 131, on the other side DT2 (lower side in FIG. 4) of the composite ceramic layer 111 with respect to the thickness direction, the first conductor layer 150, an introduction path formation layer 170, and a heater layer 180 are sequentially laminated together.

Meanwhile, the second conductor layer 155 and a protection layer 160 are laminated together on the one side DT1 (upper side in FIG. 4) of the composite ceramic layer 111.

The composite ceramic layer 111 includes the rectangular plate-like insulation portion 112 formed of alumina and having a through hole 112h which extends therethrough in the thickness direction DT and has a rectangular shape as viewed in plane, and a plate-like electrolyte portion 131 formed of oxygen ion conductive zirconia ceramic and disposed within the through hole 112h of the insulation portion 112 (see FIG. 3). The insulation portion 112 has a first insulation main surface 113 orthogonal to (intersecting with) the thickness direction DT; specifically, facing the thickness-direction other side DT2 (lower side in FIGS. 3 and 4), and a second insulation main surface 114 facing the thickness-direction one side DT1 (upper side in FIGS. 3 and 4). The insulation portion 112 also has a through-hole inner perimetric surface 115 (see FIGS. 5 and 6) which defines the through hole 112h. The electrolyte portion 131 has a first electrolyte main surface 133 orthogonal to (intersecting with) the thickness direction DT; specifically, facing the thickness-direction other side DT2, and a second electrolyte main surface 134 facing the thickness-direction one side DT1. The electrolyte portion 131 also has an electrolyte outer perimetric surface 135 (see FIGS. 5 and 6) in close contact with the through-hole inner perimetric surface 115 of the insulation portion 112.

The first conductor layer 150 is composed of the rectangular first electrode layer 151 formed on the first electrolyte main surface 133 of the electrolyte portion 131 in such a manner as to be separated inward from the wall surface of the through hole 112h and a strip-like first extension layer 152 extending from the first electrode layer 151 toward a rear side DL2 (upper side in FIG. 2 or rightward side in FIG. 3) with respect to the longitudinal direction. That is, the first extension layer 152 extends in a continuous manner on the first electrolyte main surface 133 as well as on the first insulation main surface 113 (see FIG. 5). Notably, as will be described herein later, the first extension layer 152 extends from the first electrolyte main surface 113 onto the first insulation main surface 113 through a protruding surface 122s of a protruding portion 122.

Meanwhile, the second conductor layer 155 is composed of the rectangular second electrode layer 156 formed on the second electrolyte main surface 134 of the electrolyte portion 131 in such a manner as to be separated inward from the wall surface of the through hole 112h and a strip-like second extension layer 157 extending from the second electrode layer 156 toward the rear side DL2 (see FIGS. 2 and 3). That is, the second extension layer 157 extends in a continuous manner on the second electrolyte main surface 134 as well as on the second insulation main surface 114 (see FIG. 6).

The protection layer 160 is laminated on the one side DT1 of the composite ceramic layer 111 and covers the second conductor layer 155. The protection layer 160 is composed of a porous portion 162 which is formed of a porous ceramic and covers the second electrode layer 156 and the electrolyte portion 131 of the composite ceramic layer 111, and a protection portion 161 which is formed of a dense ceramic and overlies the insulation portion 112 of the composite ceramic layer 111 to protect the same and in which a through hole 161h is formed and accommodates the porous portion 162 therein in a surrounding manner (see FIG. 3).

Also, the aforementioned sensor pads 16 and 17 are provided on the protection portion 161 (see FIGS. 2 and 3). The sensor pad 16 electrically communicates with an end portion 152e of the first extension layer 152 located on the rear side DL2 through through holes 112m and 161m. The sensor pad 17 electrically communicates with an end portion 157e of the second extension layer 157 located on the rear side DL2 through a through hole 161n.

The introduction path formation layer 170 is formed of a dense ceramic and has an introduction groove 175 extending therethrough in the thickness direction thereof (see FIG. 3). The introduction groove 175 is surrounded by not only the introduction path formation layer 170 but also the composite ceramic layer 111 and the heater layer 180 (insulation layer 182), thereby forming an atmosphere introduction path AD for introducing the atmosphere to the first electrode layer 151. More specifically, the introduction groove 175 is composed of a reference chamber groove 176 having a rectangular shape as viewed in plane and an atmosphere flow groove 177 which is smaller in width than the reference chamber groove 176, extends toward the rear side DL2 from the reference chamber groove 176, and opens at the rear end (right end in FIG. 3) of the introduction path formation layer 170. The reference chamber groove 176 is surrounded by not only the introduction path formation layer 170 but also the electrolyte portion 131 of the composite ceramic layer 111 and the heater layer 180 to thereby form a reference chamber KS, whereas the atmosphere flow groove 177 is surrounded by not only the introduction path formation layer 170 but also the insulation portion 112 of the composite ceramic layer 111 and the heater layer 180 to thereby form an atmosphere flow path TR. Notably, the first electrode layer 151 formed on the electrolyte portion 131 is exposed to the reference chamber KS.

The heater layer 180 includes two plate-like insulation layers 182 and 183 formed of alumina and the heater pattern 181 embedded therebetween (see FIGS. 3 and 4). The heater pattern 181 is composed of a meandering heat-generating portion 181d and a first lead portion 181b and a second lead portion 181c connected to the respective opposite ends of the heat-generating portion 181d and extending rectilinearly. An end portion 181e of the first lead portion 181b located on the rear side DL2 electrically communicates with the heater pad 14 through a through hole 183m, and an end portion 181f of the second lead portion 181c located on the rear side DL2 electrically communicates with the heater pad 15 through a through hole 183n (see FIG. 3).

Thus, in the gas sensor element 10 according to the present embodiment, the atmosphere around the rear end portion 10k of the gas sensor element 10 reaches the first electrode layer 151 through the aforementioned atmosphere introduction path AD.

Meanwhile, gas to be measured around the forward end portion 10s of the gas sensor element 10 reaches the second electrode layer 156 through the porous portion 162 disposed in the through hole 161h of the protection layer 160. The through hole 161h of the protection layer 160 (protection portion 161) serves as a gas introduction path GD for introducing external gas to be measured to the second electrode layer 156, and the protection portion 161 and the porous portion 162 collectively form a gas introduction path formation member which forms the gas introduction path GD.

Notably, since the electrolyte portion 131 is disposed between the first electrode layer 151 and the second electrode layer 156, in the case where the atmosphere in contact with the first electrode layer 151 and gas to be measured in contact with the second electrode layer 156 differ in oxygen concentration, the first electrode layer 151, the electrolyte portion 131, and the second electrode layer 156 constitute an oxygen concentration cell, and an electrical potential difference is generated between the first electrode layer 151 and the second electrode layer 156. By use of the electrical potential difference, the gas sensor 1 of the present embodiment detects the oxygen concentration in gas to be measured.

Figure 5:
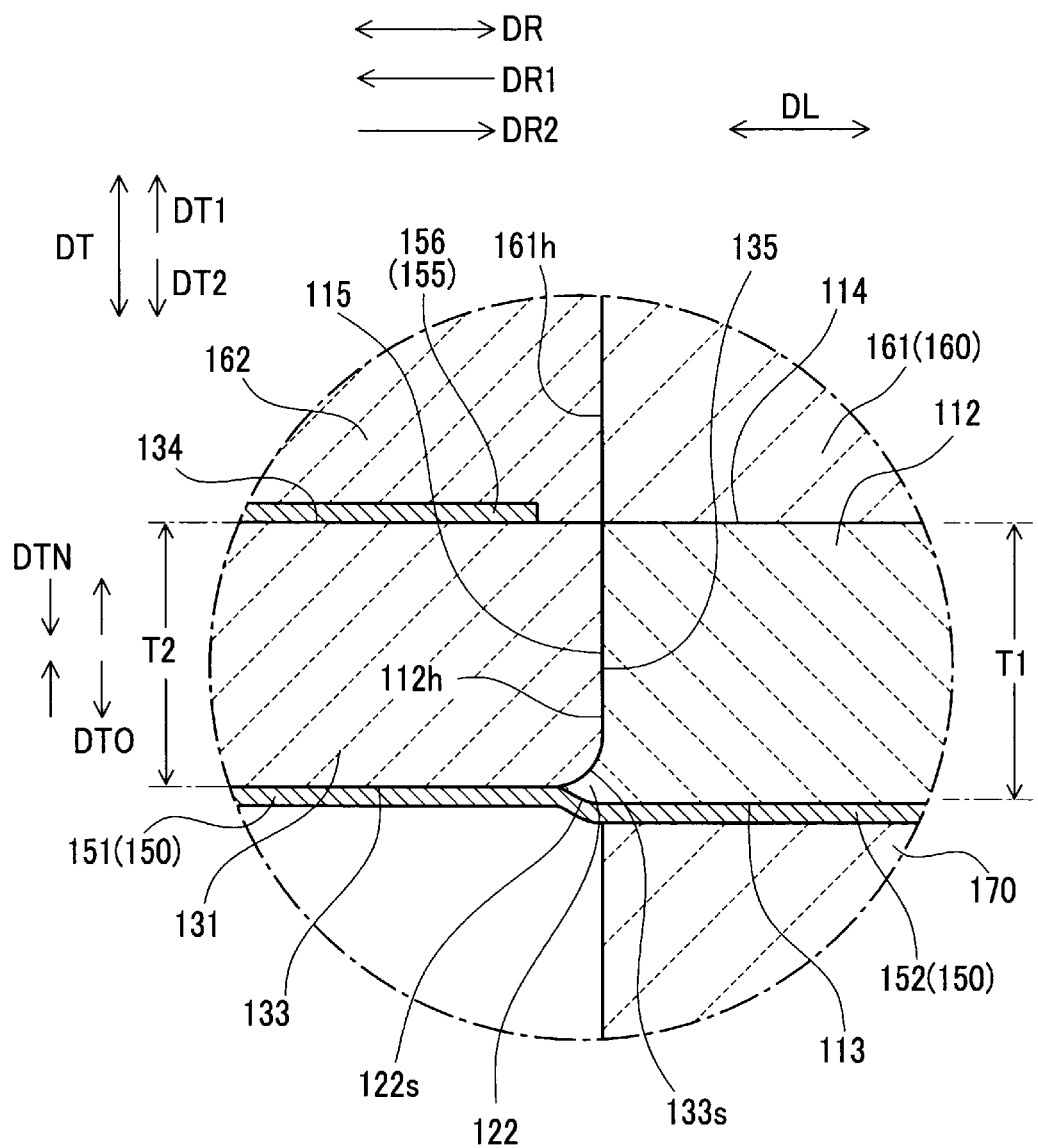
FIG. 5 is an enlarged sectional view (sectional view taken along line C-C of FIG. 2) of the gas sensor element according to the embodiment.
Figure 6:
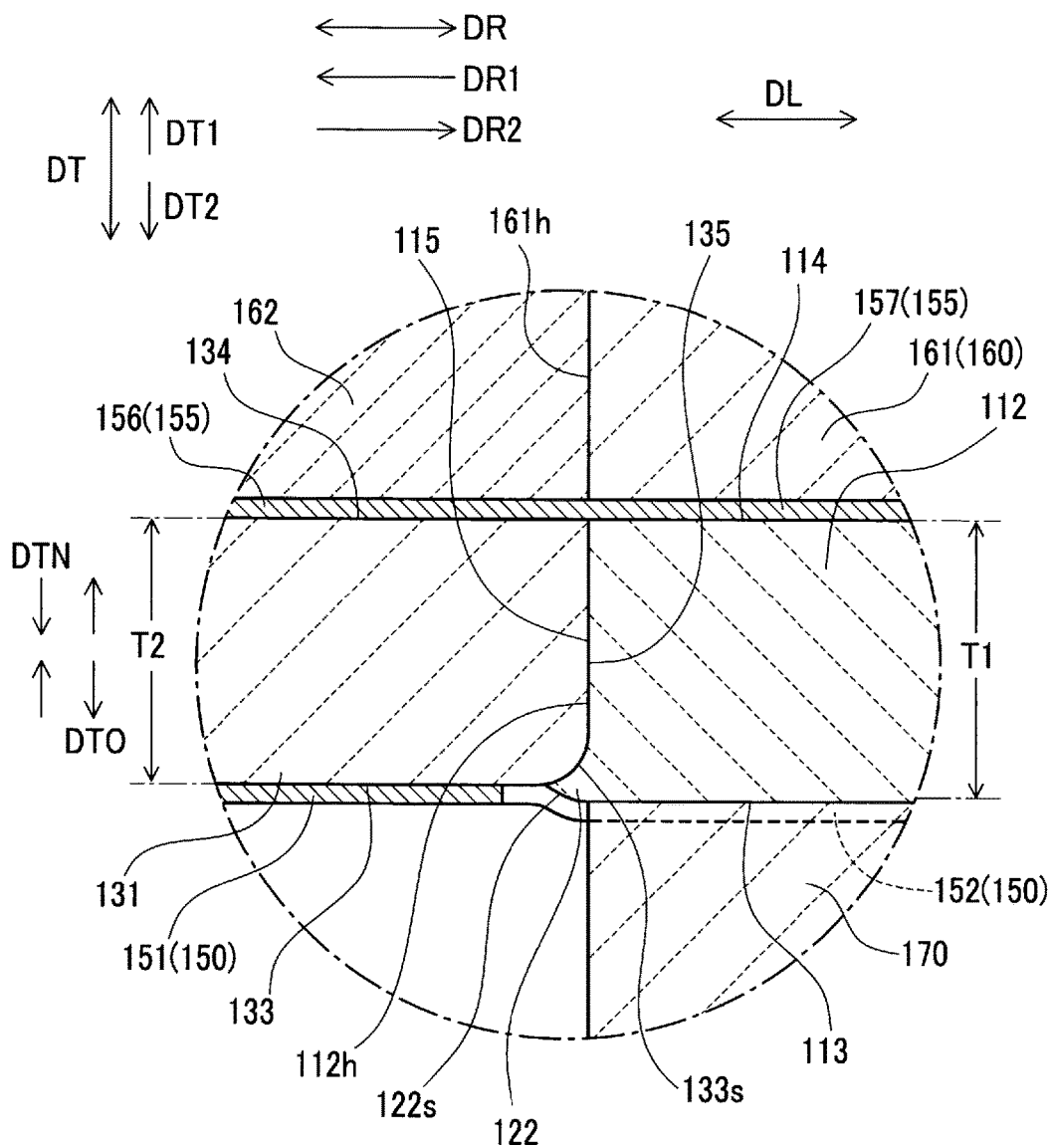
FIG. 6 is an enlarged sectional view (sectional view taken along line D-D of FIG. 2) of the gas sensor element according to the embodiment.

Next, in the gas sensor element 10 according to the present embodiment, the boundary and its periphery between the insulation portion 112 and the electrolyte portion 131 of the composite ceramic layer 111 will be described in detail. In the present embodiment, as shown in FIGS. 5 and 6, the thickness T2 of the electrolyte portion 131 is smaller than the thickness T1 of the insulation portion 112 (T2<T1). The thickness T2 of the electrolyte portion 131 has a great effect on properties of an oxygen concentration cell which the electrolyte portion 131 partially constitutes. Meanwhile, as will be described herein later, in the course of manufacture of the gas sensor 1 (gas sensor element 10), a green composite layer 211 is compressed in the thickness direction DT. Thus, by means of employing a thin electrolyte green sheet which is to become the electrolyte portion 131, in the course of compression, pressure is unlikely to be applied to the electrolyte portion 131, so that variation is unlikely to arise in the thickness T2. Therefore, variations in properties stemming from variations in the thickness T2 of the electrolyte portion 131 can be suppressed among the gas sensor elements 10.

Also, the second electrolyte main surface 134 of the electrolyte portion 131 is flush with the second insulation main surface 114 of the insulation portion 112 (see FIGS. 5 and 6). By contrast, the first electrolyte main surface 133 of the electrolyte portion 131 is located on the thickness-direction one side DT1 (thickness-direction inward side DTN or upper side in FIGS. 5 and 6) with respect to the first insulation main surface 113 of the insulation portion 112.

The insulation portion 112 has, on a first insulation main surface 113 side, the protruding portion 122 overlying the first electrolyte main surface 133 of the electrolyte portion 131 and protruding toward the inward side DR1 of the through hole 112h (see FIGS. 2, 5, and 6). The protruding portion 122 has such a form as to reduce in thickness toward the inward side DR1 of the through hole 112h (as it progresses leftward in FIGS. 5 and 6); i.e., a tapering form. Notably, in the present embodiment, the protruding portion 122 is formed along the entire perimeter of the through hole 112h.

Furthermore, the first insulation main surface 113 of the insulation portion 112 has a form in which the protrusion surface 122s of the protruding portion 122 progresses toward the thickness-direction inward side DTN (herein, toward the thickness-direction one side DT1) and approaches the first electrolyte main surface 133 as it progresses toward the inward side DR1 of the through hole 112h. That is, the protrusion surface 122s of the protruding portion 122 is a gentle slope which progresses upward as it progresses leftward in FIG. 5, and the level difference between the first insulation main surface 113 of the insulation portion 112 and the first electrolyte main surface 133 of the electrolyte portion 131 is mitigated at the protruding portion 122. Therefore, the first extension layer 152 of the first conductor layer 150 gently extends in the longitudinal direction DL.

Thus, in the gas sensor element 10 according to the present embodiment, the first conductor layer 150 (first extension layer 152) extending in a continuous manner on the protrusion surface 122s of the protruding portion of the first insulation main surface 113 as well as on the first electrolyte main surface 133 is unlikely to suffer cracking or breaking at a portion on the boundary between the protrusion surface 122s of the protruding portion of the first insulation main surface 113 and the first electrolyte main surface 133, whereby the gas sensor element 10 provides high reliability.

Furthermore, an overlying surface 133s of the first electrolyte main surface 133 which the protruding portion 122 overlies from the thickness-direction outward side DTO (thickness-direction other side DT2) has such a form as to extend toward the outward side DR2 of the through hole 112h as well as toward the thickness-direction inward side DTN (herein, thickness-direction one side DT1). That is, the overlying surface 133s approaches the second electrolyte main surface 134; i.e., inclination thereof increases, as it progresses toward the outward side DR2. In the present embodiment, specifically, the overlying surface 133s of the first electrolyte main surface 133 has such a form as to be rounded in the form of an arc convexed toward the outward side DR2 and toward the obliquely thickness-direction outward side DTO (lower right in FIG. 5).

That is, in the gas sensor element 10, the overlying surface 133s of the first electrolyte main surface 133 which the protruding portion 122 of the insulation portion 112 overlies is deformed in the form of an arc, whereby the protruding portion 122 of the insulation portion 112 is in close contact with the overlying surface 133s of the electrolyte portion 131. Thus, an angular portion is not formed in a region of the electrolyte portion 131 which the protruding portion 122 overlies, whereby there can be restrained the occurrence of cracking in the protruding portion 122 starting from any portion of the overlying surface 133s.

Since the electrolyte portion 131 is formed by firing a green electrolyte portion 231 (which will be described herein later) formed of an electrolyte green sheet, which allows easy control of thickness in the course of manufacturing the sheet (before firing) and after firing, the thickness T2 of the electrolyte portion 131 can be rendered uniform among products; thus, properties of an oxygen concentration cell composed of the electrolyte portion 131, the first electrode layer 151, and the second electrode layer 156 can be rendered uniform among the gas sensor elements 10.

Furthermore, in the present embodiment, since the electrolyte portion 131 is thinner than the insulation portion 112 (T2<T1), although pressure is applied in the thickness direction DT to a green composite layer 211 for close contact between and lamination of the green electrolyte portion 231 and a green insulation portion 212 in the course of manufacture, pressure is unlikely to be applied to the green electrolyte portion 231 which is to become the electrolyte portion 131; thus, variation is unlikely to arise in the thickness of the electrolyte portion 131, which would otherwise result from compression. Therefore, variations in properties can be further reduced among the gas sensor elements 10.

Also, as shown in FIG. 6, the second electrolyte main surface 134 of the electrolyte portion 131 and the second insulation main surface 114 of the insulation portion 112 are flush with each other. Thus, the second conductor layer 155 (second extension layer 157) extending in a continuous manner on the second electrolyte main surface 134 as well as on the second insulation main surface 114 extends in the longitudinal direction DL without involvement of a level difference and is thus unlikely to suffer the occurrence of cracking or breaking at a portion on the boundary between the second electrolyte main surface 134 and the second insulation main surface 114, so that the gas sensor element 10 provides high reliability.

Also, in the gas sensor element 10 of the present embodiment, the first electrode layer 151, the second electrode layer 156, and the electrolyte portion 131 intervening therebetween constitute an oxygen concentration cell, and gas to be measured is brought in contact with the second electrode layer 156, whereas the atmosphere (reference gas) is brought in contact with the first electrode layer 151. In such a gas sensor, the magnitude (variation) of the thickness of the second electrode layer 156 in contact with gas to be measured has a greater effect on properties of the gas sensor element 10 as compared with the magnitude (variation) of the thickness of the first electrode layer 151 in contact with reference gas.

In the gas sensor element 10 of the present embodiment, the first electrode layer 151 is formed on the first electrolyte main surface 133 which is located on the thickness-direction inward side DTN with respect to the first insulation main surface 113. Thus, as will be described herein later, in the case where the first electrode layer 151 is formed by screen-printing electrode paste on the first electrolyte main surface 133 depressed from the surrounding first insulation main surface 113, followed by firing, difficulty is encountered in controlling the thickness of the first electrode layer 151 (electrode paste); as a result, the thickness is apt to vary among products.

Meanwhile, the second electrode layer 156 of the gas sensor element 10 is formed on the second electrolyte main surface 134 which is disposed flush with the second insulation main surface 114. Thus, in screen printing a green second electrode layer 256 (which will be described herein later) which is to become the second electrode layer 156 after firing, the thickness of electrode paste (green second electrode layer 256) can be readily controlled. Thus, among the gas sensor elements 10 in which reference gas (the atmosphere) is in contact with the first electrode layer 151, whereas gas to be measured is in contact with the second electrode layer 156, variations in properties of the oxygen concentration cell can be suppressed, and properties of the oxygen concentration cell can be rendered uniform.

In the gas sensor element 10 according to the present embodiment, gas to be measured which is introduced through the porous portion 162, which serves as the gas introduction path, comes into contact with the second electrode layer 156, whereas the atmosphere introduced through the atmosphere introduction path AD comes into contact with the first electrode layer 151. Thus, by use of an electromotive force generated in response to the oxygen concentration difference between gas to be measured in contact with the second electrode layer 156 and the atmosphere in contact with the first electrode layer 151, whether or not oxygen exists in gas to be measured can be detected.

Also, because of employment of the above-mentioned gas sensor element 10, the gas sensor 1 according to the present embodiment is unlikely to suffer the occurrence of cracking or breaking of the first conductor layer 150 (first extension layer 152) and thus provides high reliability.

Next, a method of manufacturing the gas sensor 1 according to the present embodiment will be described with reference to the drawings. First, a green insulation-portion sheet 212s (insulation green sheet) having a thickness of 230 µm and a green electrolyte-portion sheet 231s (electrolyte green sheet) having a smaller thickness of 200 µm are prepared beforehand by the doctor blade process.

Next, a sheet through hole 212h is formed in the green insulation-portion sheet 212s in such a manner as to extend therethrough in a sheet thickness direction ST (through hole forming step). The through hole forming step uses a lower die 301 made of metal and having a lower-die working hole 302, an upper die 303 made of metal and having an upper-die working hole 304, and a punch 305 made of metal (see FIG. 7A). The lower-die working hole 302, the upper-die working hole 304, and the punch 305 each have a rectangular section having a radiused corner.

Figure 7A:
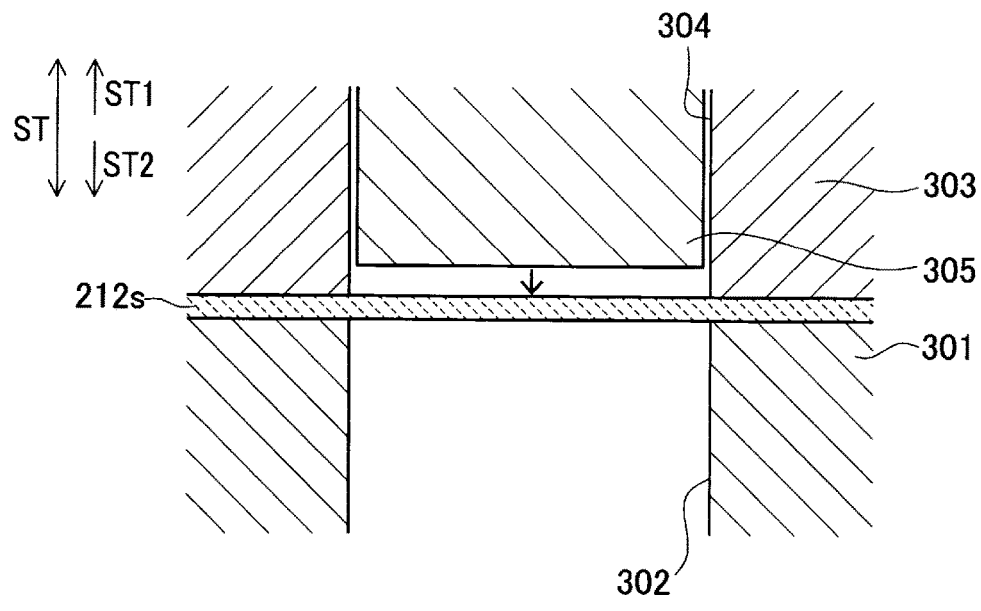
FIGS. 7A and 7B are explanatory views showing a through hole forming step in a method of manufacturing a gas sensor element according to the embodiment and a modified embodiment.

First, the green insulation-portion sheet 212s is disposed on the lower die 301 in such a manner as to cover the lower-die working hole 302 (see FIG. 7A). Next, the upper die 303 is disposed on the green insulation-portion sheet 212s to hold the green insulation-portion sheet 212s between the upper die 303 and the lower die 301; subsequently, the punch 305 is inserted into the working holes 302 and 304 to punch out a relevant portion of the green insulation-portion sheet 212s (see FIG. 7B), thereby forming the green insulation portion 212 having a sheet through hole 212h (see FIG. 8).

The green insulation portion 212 is to become the aforementioned insulation portion 112 of the composite ceramic layer 111 after a firing step, which will be described herein later. The green insulation portion 212 has a first insulation sheet main surface 213 facing the sheet thickness-direction other side ST2, a second insulation sheet main surface 214 facing the sheet thickness-direction one side ST1, and a sheet through hole 212h. The inner perimetric surface of the sheet through hole 212h of the green insulation portion 212 is called a sheet through-hole inner perimetric surface 215 (see FIG. 8).

Figure 7B:
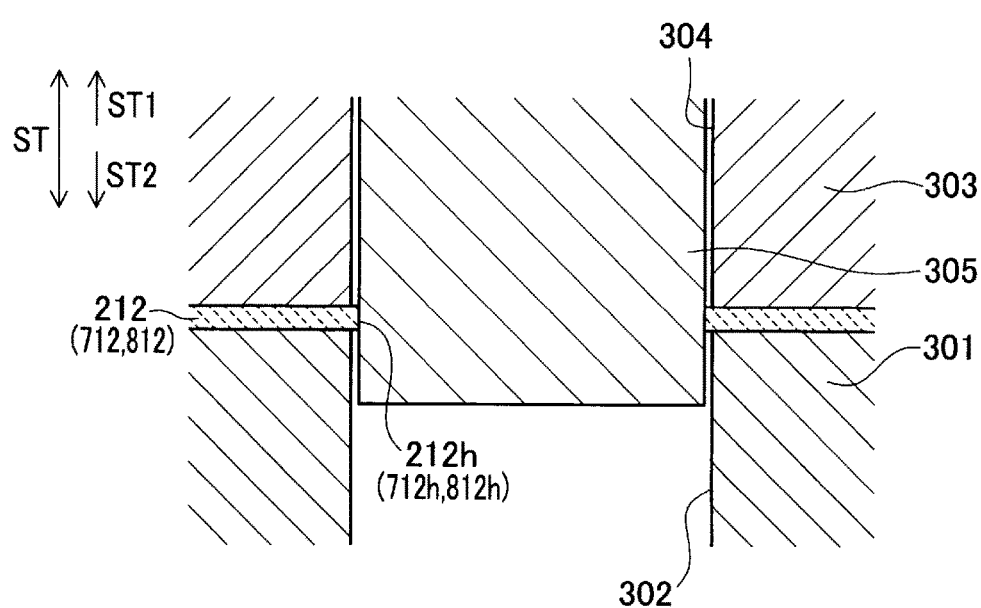
Figure 8:
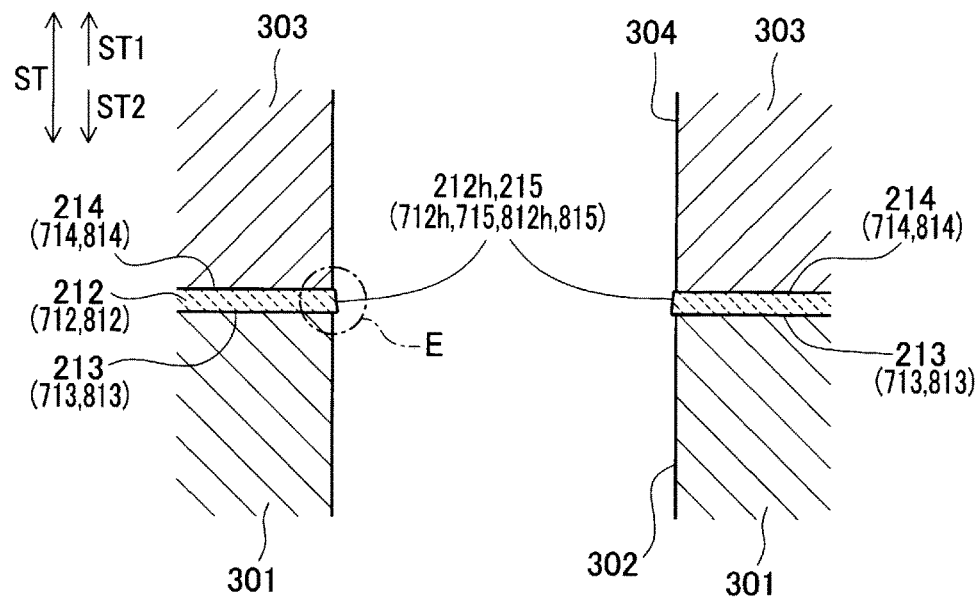
FIG. 8 is an explanatory view showing the through hole forming step in the method of manufacturing a gas sensor element according to the embodiment and the modified embodiment.
Figure 9:
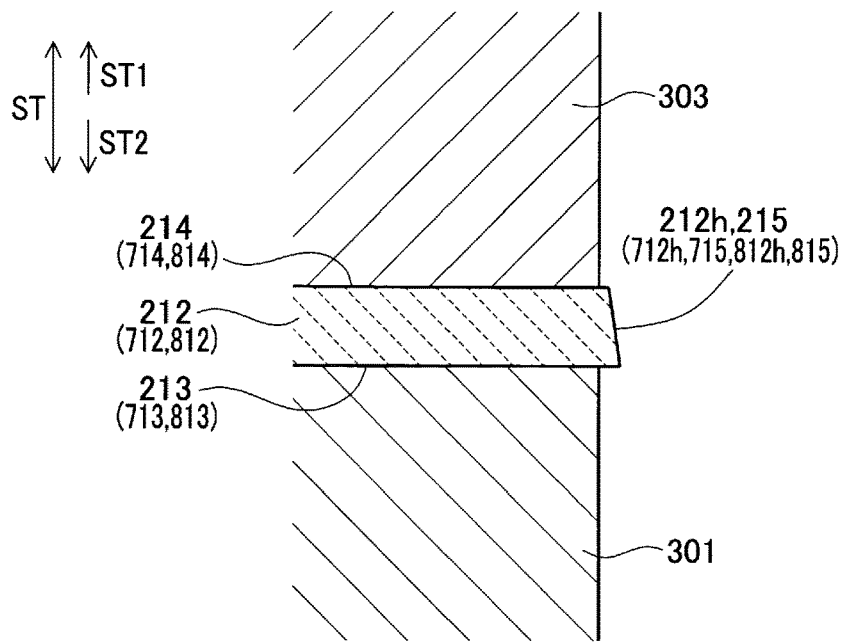
FIG. 9 is an explanatory view showing the through hole forming step in the method of manufacturing a gas sensor element according to the embodiment and the modified embodiment.

The sheet through hole 212h has a form of tapering toward the other side ST2 (in FIG. 8, toward the lower side). For example, as shown in FIG. 9, which is an enlarged sectional view of region E of FIG. 8, the sheet through hole 212h has a form in which the inner perimetric surface 215 is inclined in such a manner as to face the upper right in FIG. 9. This is for the following reason: as shown in FIG. 7A and FIG. 7B, the external dimension (size) of the punch 305 is slightly smaller as compared with the lower-die working hole 302 and the upper-die working hole 304, so that a gap is formed therebetween.

Subsequently, by use of the dies 301, 303, and 305, an inserting step is performed for inserting the green electrolyte portion 231 into the sheet through hole 212h of the green insulation portion 212 (see FIG. 10A and FIG. 10B). The green electrolyte-portion sheet 231s is placed on the green insulation portion 212 disposed on the lower die 301. Next, the green insulation portion 212 and the green electrolyte-portion sheet 231s are held between the lower die 301 and the upper die 303 (see FIG. 10A). A lower surface 305B of the punch 305 is slightly lowered toward the other side ST2 (toward the lower side in FIG. 10A and FIG. 10B) with respect to a lower surface 303B of the upper die 303 to punch out the green electrolyte portion 231 from the green electrolyte-portion sheet 231s and to insert the green electrolyte portion 231 into the sheet through hole 212h of the green insulation portion 212. More specifically, as shown in FIG. 10B, the punch 305 is moved toward the other side ST2 until the lower surface 305B of the punch 305 reaches a position located below the lower surface 303B of the upper die 303 and above the second insulation sheet main surface 214 of the green insulation portion 212. By this procedure, the green electrolyte portion 231 is inserted into the sheet through hole 212h in such a manner that a second electrolyte sheet main surface 234 of the green electrolyte portion 231 facing the one side ST1 (upper side in FIG. 10A and FIG. 10B) is located (protrudes) on the one side ST1 (sheet thickness-direction outward side STO) with respect to the second insulation sheet main surface 214 of the green insulation portion 212, while a first electrolyte sheet main surface 233 facing the other side ST2 (lower side in FIG. 10A and FIG. 10B) is located on the one side ST1 (sheet thickness-direction inward side STN) with respect to the first insulation sheet main surface 213 of the green insulation portion 212 (see FIG. 10B).

Figure 11:
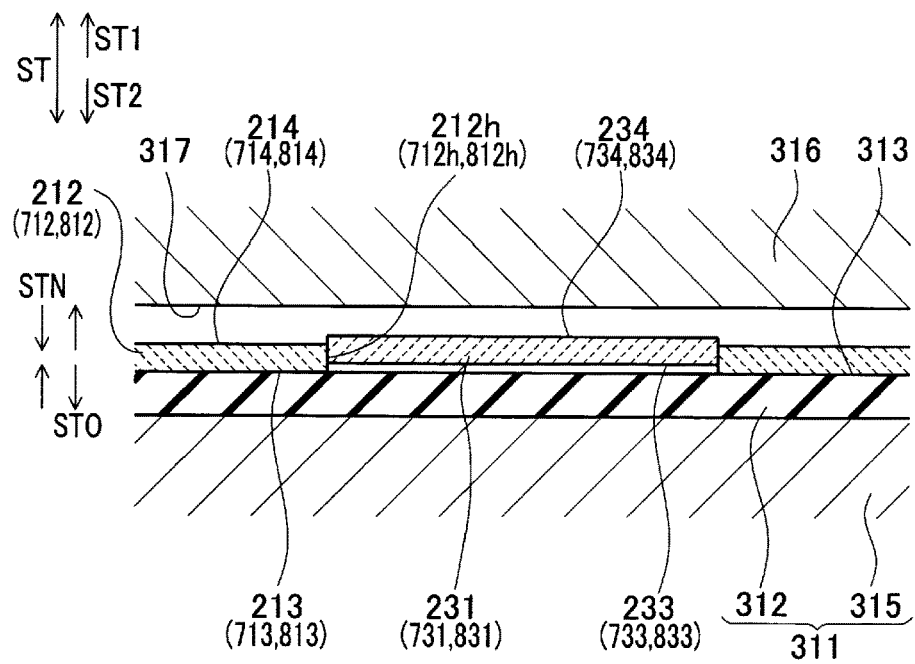
FIG. 11 is an explanatory view showing a compressing step in the method of manufacturing a gas sensor element according to the embodiment and the modified embodiment.

Next, a compressing step is performed (see FIG. 11). In the compressing step, the green insulation portion 212 is compressed in the sheet thickness direction ST to bring the green insulation portion 212 and the green electrolyte portion 231 inserted in the sheet through hole 212h into close contact with each other. The compressing step uses a first compression die 311 having a flat first compression surface 313 and a second compression die 316 having a flat second compression surface 317. The first compression die 311 has a rubber plate member 312 formed of a rectangular plate-like rubber (elastic rubber member) and having the flat first compression surface 313, and a body member 315 adapted to support the rubber plate member 312. The second compression die 316 is a metal member and can move in the vertical direction in FIG. 11.

First, the green insulation portion 212 and the green electrolyte portion 231 inserted in the sheet through hole 212h are disposed on the first compression die 311 in such a manner that the first electrolyte sheet main surface 233 and the first insulation sheet main surface 213 face the first compression surface 313 (downward in FIG. 11). Then, the second compression die 316 is moved from the one side ST1 (upper side in FIG. 11) toward the other side ST2 (lower side) to compress the green insulation portion 212 in the sheet thickness direction ST between the first compression surface 313 and the second compression surface 317, thereby forming the green composite layer 211 (see FIG. 12).

Figure 12:
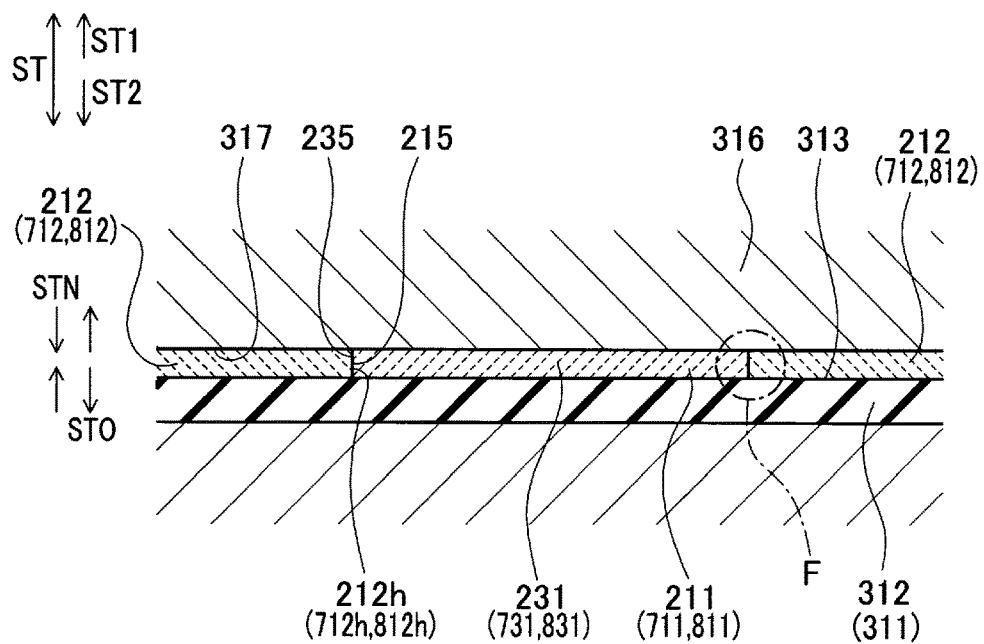
FIG. 12 is an explanatory view showing the compressing step in the method of manufacturing a gas sensor element according to the embodiment and the modified embodiment.
Figure 13:
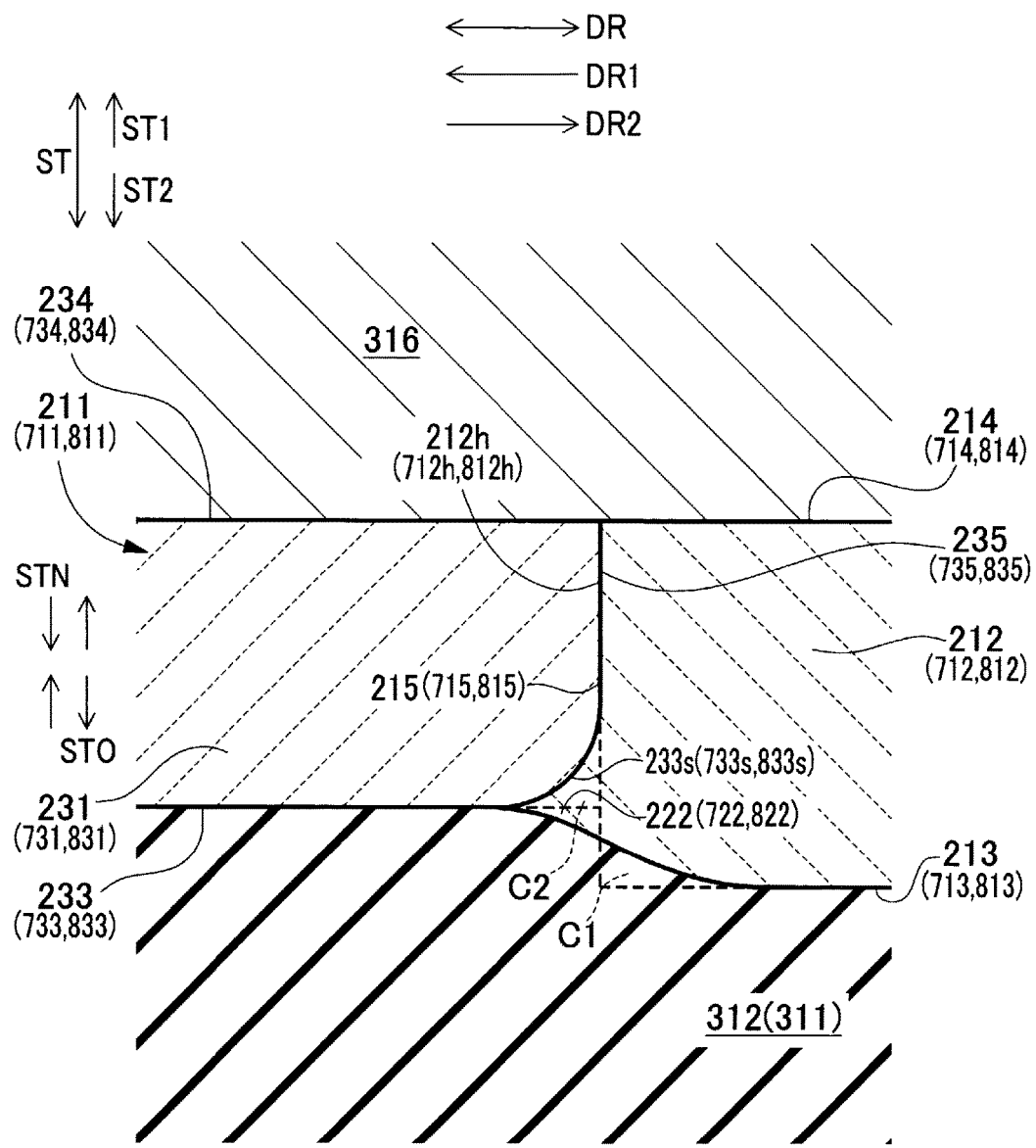
FIG. 13 is an explanatory view showing the compressing step in the method of manufacturing a gas sensor element according to the embodiment and the modified embodiment.

Since the second compression die 316 is formed of a flat metal, the protruding green electrolyte portion 231 is pressed into the sheet through hole 212h, whereby the second insulation sheet main surface 214 of the green insulation portion 212 and the second electrolyte sheet main surface 234 of the green electrolyte portion 231 become flush with each other (see FIGS. 12 and 13). By contrast, the first electrolyte sheet main surface 233 of the green electrolyte portion 231 is located on the one side ST1 (inward side STN); i.e., within the sheet through hole 212h.

As mentioned above, since the green insulation portion 212 is thicker than the green electrolyte portion 231, the green insulation portion 212 is strongly compressed. Accordingly, the green insulation portion 212 extends in an extending direction (horizontal direction in FIG. 13) orthogonal to the sheet thickness direction ST and is deformed in such a manner that the sheet through hole 212h shrinks. Thus, the sheet through-hole inner perimetric surface 215 of the green insulation portion 212 comes in close contact with an electrolyte sheet outer perimetric surface 235 of the green electrolyte portion 231.

Furthermore, since the rubber plate member 312 of the first compression die 311 is formed of elastic rubber, as a result of compression, the rubber plate member 312 is deformed. That is, as shown on an enlarged scale in FIG. 13, the rubber plate member 312 presses the green insulation portion 212, and a portion which faces the first electrolyte sheet main surface 233 of the green electrolyte portion 231 is deformed and enters the sheet through hole 212h in such a manner as to come into contact with the first electrolyte sheet main surface 233.

As a result of this deformation and compression of the rubber plate member 312, the green electrolyte portion 231 and the green insulation portion 212 are also deformed accordingly.

Specifically, a corner portion C1 (a portion indicated by the broken line in FIG. 13) of the green insulation portion 212 located on the first insulation sheet main surface 213 side and defined by the sheet through-hole inner perimetric surface 215 and the first insulation sheet main surface 213 enters the sheet through hole 212h and is deformed in such a manner as to cover the green electrolyte portion 231, thereby becoming a green protruding portion 222. The green protruding portion 222 is to become the protruding portion 122 of the insulation portion 112 after firing and has such a form as to overlie the first electrolyte sheet main surface 233 of the green electrolyte portion 231, to protrude toward the inward side DR1 (leftward side in FIG. 13) of the sheet through hole 212h, and to reduce in thickness toward the inward side DR1.

Furthermore, in association with deformation of the corner portion C1, a corner portion C2 (a portion indicated by the broken line in FIG. 13) of the green electrolyte portion 231 which faces the sheet through-hole inner perimetric surface 215 and is defined by the electrolyte sheet outer perimetric surface 235 and the first electrolyte sheet main surface 233 is also deformed. Specifically, an overlying surface 233s of the first electrolyte sheet main surface 233 which the green protruding portion 222 overlies from the sheet thickness-direction outward side STO (the other side ST2) has such a form as to extend toward the outward side DR2 of the sheet through hole 212h as well as toward the sheet thickness-direction inward side DTN (herein, the sheet thickness-direction one side ST1). In the present embodiment, the corner portion C2 is deformed in such a manner as to be rounded to a quarter of a circle convexed outward.

Next, a first printing step is performed. In the first printing step, a green first conductor layer 250 (a green first electrode layer 251 and a green first extension layer 252) is formed by screen printing in such a manner as to extend in a continuous manner on the first electrolyte sheet main surface 233 of the green electrolyte portion 231 as well as on the first insulation sheet main surface 213 of the green insulation portion 212 (see FIG. 14). Notably, the green first conductor layer 250 (green first extension layer 252) is connected to a through hole 112m extending through the green insulation portion 212 (see FIG. 15).

Subsequently, a second printing step is performed. In the second printing step, a green second conductor layer 255 (a green second electrode layer 256 and a green second extension layer 257) is formed by screen printing in such a manner as to extend in a continuous manner on the second electrolyte sheet main surface 234 of the green electrolyte portion 231 as well as on the second insulation sheet main surface 214 of the green insulation portion 212 (see FIG. 14).

Figure 15:
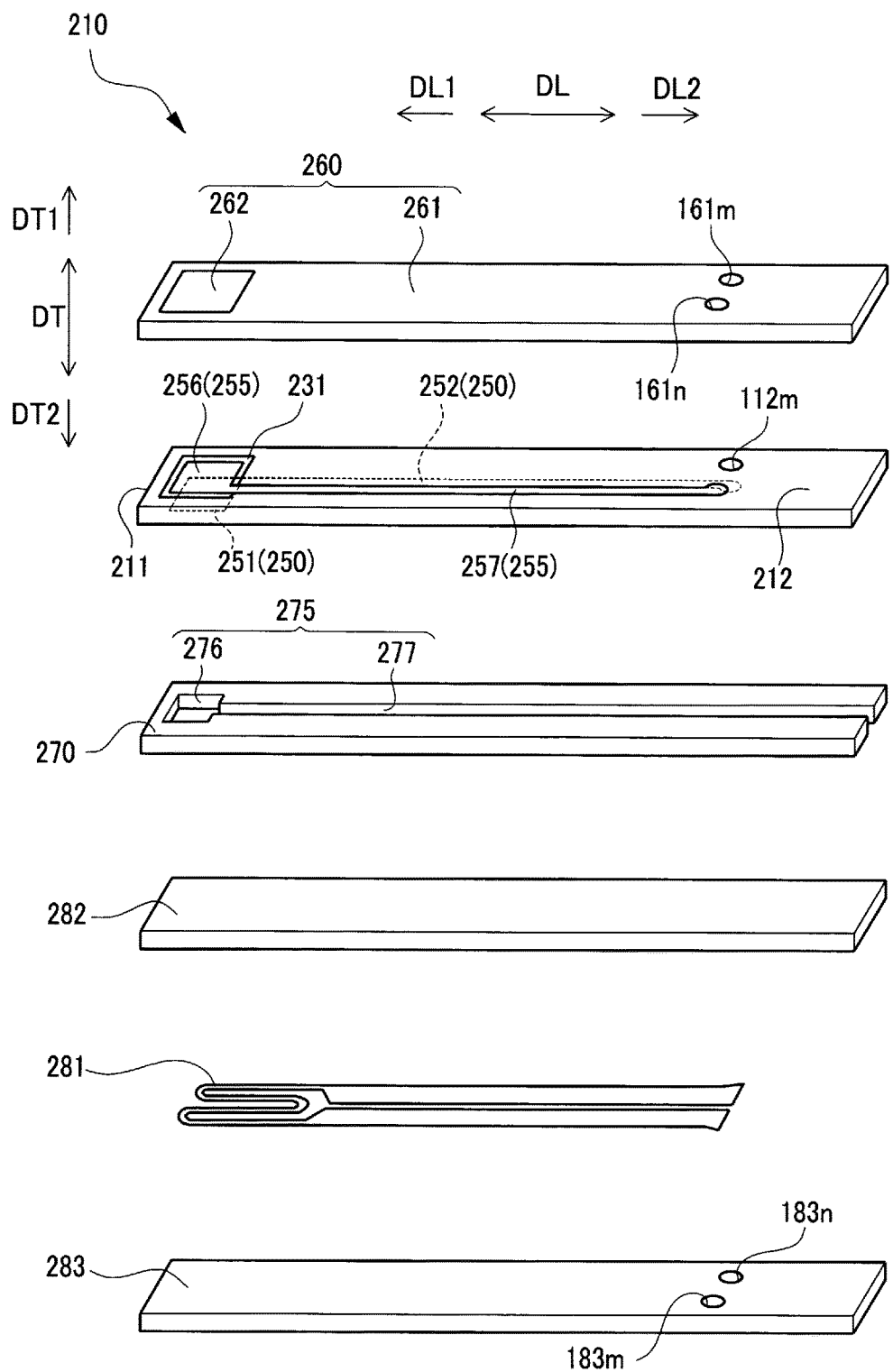
FIG. 15 is an explanatory view for explaining the method of manufacturing a gas sensor element according to the embodiment.

Next, as shown in FIG. 15, green insulation layers 283 and 282, a green introduction path formation layer 270, the green composite layer 211, and a green protection layer 260 are sequentially laminated together, thereby forming a green laminate 210. Notably, a green heater pattern 281 and the through holes 183m and 183n are formed beforehand on and in the green insulation layer 283. A green introduction groove 275 including a green reference chamber groove 276 and a green atmosphere flow groove 277 is formed beforehand in the green introduction path formation layer 270. The green protection layer 260 is composed of a green porous portion 262 which is to become the porous portion 162 after firing, and a green protection portion 261 which surrounds the green porous portion 262 and is to become the protection portion 161 after firing. The through holes 161m and 161n which extend through the green protection portion 261 and are connected to the through hole 112m and the green second conductor layer 255, respectively, are formed beforehand at the rear side DL2 of the green protection layer 260. Also, green pads (not shown) which are to become the heater pads 14 and 15 and the sensor pads 16 and 17 after firing are printed on the green laminate 210.

Next, by a publicly known method, the green laminate 210 (see FIG. 15) is fired, thereby forming the gas sensor element 10 which includes the composite ceramic layer 111, the first conductor layer 150, and the second conductor layer 155 (see FIGS. 2 to 4).

In the method of manufacturing the gas sensor element 10 according to the present embodiment, the compressing step compresses the green insulation portion 212 in the sheet thickness direction ST to shrink the sheet through hole 212h, thereby bringing the sheet through-hole inner perimetric surface 215 into close contact with the electrolyte sheet outer perimetric surface 235 of the green electrolyte portion 231.

Furthermore, by means of forming the green protruding portion 222, the composite ceramic layer 111 after firing can readily have the protruding portion 122 (see FIG. 5). Thus, there can be manufactured the highly reliable gas sensor element 10 in which the first conductor layer 150 formed by firing the green first conductor layer 250 is unlikely suffer the occurrence of cracking or breaking at a position between the first electrolyte main surface 133 and the first insulation main surface 113.

According to the manufacturing method, the compressing step forms the green overlying surface 233s of the first electrolyte sheet main surface 233 of the green electrolyte portion 231 into such a form as to extend toward the outward side DR2 of the sheet through hole 212h as well as toward the sheet thickness-direction inward side STN. Thus, in the composite ceramic layer 111 after firing, there can be appropriately restrained the occurrence of cracking in the protruding portion 122 starting from any portion of the overlying surface 133s.

The inserting step inserts the green electrolyte portion 231 into the sheet through hole 212h in such a manner that the green electrolyte portion 231 protrudes toward the sheet thickness-direction one side ST1 (sheet thickness-direction outward side STO) with respect to the second insulation sheet main surface 214 of the green insulation portion 212. Thus, in the compressing step, the flat second compression surface 317 of the second compression die 316 presses the protruding green electrolyte portion 231 into the sheet through hole 212h, whereby the second electrolyte sheet main surface 234 of the green electrolyte portion 231 can be readily rendered flush with the second insulation sheet main surface 214 of the green insulation portion 212. Thus, there can be easily formed the gas sensor element 10 having the composite ceramic layer 111 in which the second electrolyte main surface 134 of the electrolyte portion 131 is flush with the second insulation main surface 114 of the insulation portion 112.

By virtue of this, there can be manufactured the gas sensor element 10 having higher reliability in which the second conductor layer 155 formed by firing the green second conductor layer 255 extending in a continuous manner on the second insulation main surface 114 as well as on the second electrolyte main surface 134, also, is unlikely to suffer the occurrence of cracking or breaking at a portion on the boundary between the two main surfaces.

Furthermore, since the second electrolyte sheet main surface 234 is flush with the second insulation sheet main surface 214, the thickness of the green second conductor layer 255 formed by screen printing, and, in turn, the thickness of the second conductor layer 155 (particularly, the thickness of the second electrode layer 156 on the second electrolyte main surface 134) after firing can be easily controlled.

(Modified Embodiment)

Next, a gas sensor 401 according to a modified embodiment will be described with reference to FIGS. 7 to 14 and 16 to 23. The gas sensor 401 of the present modified embodiment differs from the gas sensor 1 of the embodiment using the one-cell type element 10 in that the gas sensor 401 uses a so-called two-cell type gas sensor element 410 including two composite ceramic layers (a detection-use composite ceramic layer 511 and a pump-use composite ceramic layer 611, which will be described herein later). Thus, the present modified embodiment will be described centering on points of difference from the embodiment, and description of similar constitutional features will be omitted or briefed. Similar constitutional features yield similar actions and effects. In the following description, like members or portions are denoted by like reference numerals.

Figure 16:
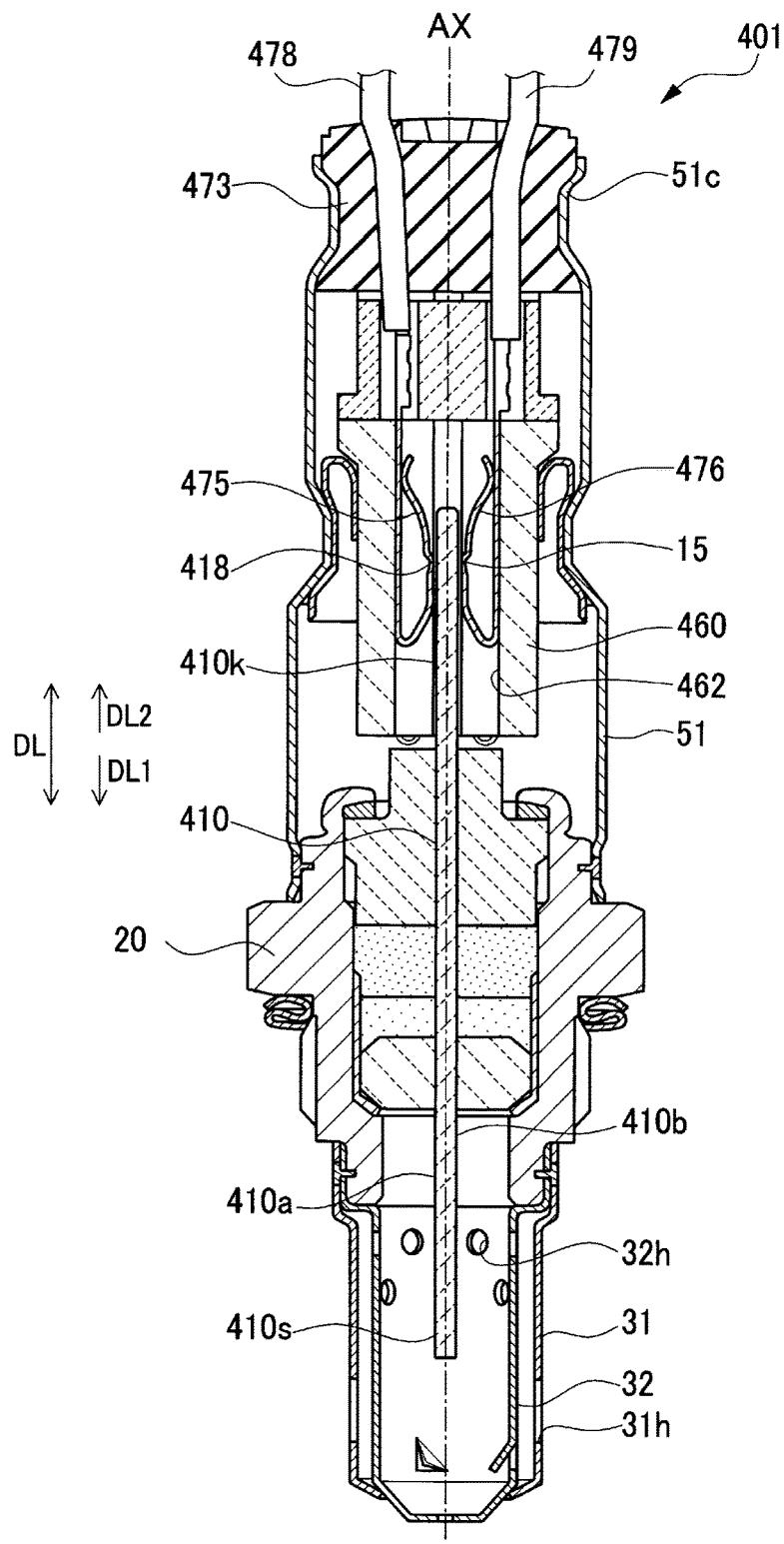
FIG. 16 is a longitudinal sectional view of a gas sensor according to a modified embodiment.

As shown in FIG. 16, the gas sensor 401 has a form similar to that of the gas sensor 1 and includes the gas sensor element 410 and the metallic shell 20 for holding therein the gas sensor element 410. Different from the gas sensor 1 of the embodiment, the gas sensor element 410 includes five pads 14, 15, 416, 417, and 418; thus, a separator 460 holds five terminal members 475, 475, 476, 476, and 476 which are elastically in contact with the pads 14, 15, 416, 417, and 418, respectively (see FIGS. 16 to 19). In the gas sensor 1 of the embodiment, the metal pipe 74 covered with the filter 74*f* is fitted into the grommet 73; however, a grommet 473 of the present modified embodiment is not provided with a filter or the like. That is, the atmosphere around the gas sensor 401 is not introduced into the gas sensor 401.

Figure 17:
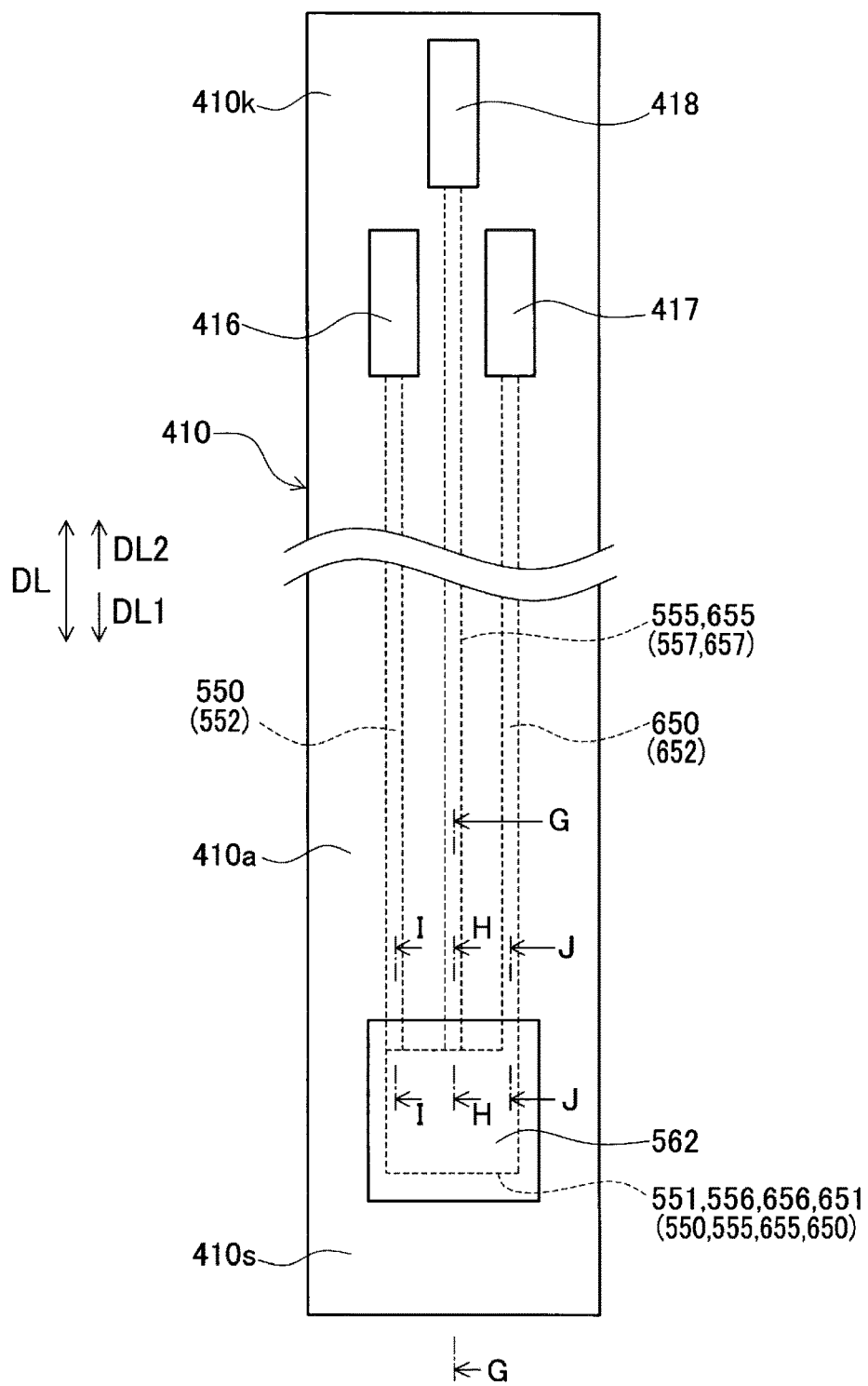
FIG. 17 is a plan view of the gas sensor element according to the modified embodiment.

The gas sensor element 410 also has a rectangular plate-like form elongated in the longitudinal direction DL (vertical direction in FIGS. 16 and 17). The gas sensor element 410 is also disposed within the gas sensor 401 with its center line coinciding with the axial line AX (see FIG. 16). The gas sensor element 410 has two heater pads 14 and 15 formed on a second element main surface 410*b* facing the thickness-direction other side DT2 (lower side in FIGS. 18 and 19) at a rear end portion 410*k*. Also, the gas sensor element 410 has three sensor pads 416, 417, and 418 on a first element main surface 410*a* facing the thickness-direction one side DT1 (upper side in FIGS. 18 and 19) at the rear end portion 410*k*.

The gas sensor element 410 is also composed of a plurality of ceramic layers and conductor layers laminated together in the thickness direction DT. Specifically, the gas sensor element 410 has the detection-use composite ceramic layer 511 used for detecting oxygen concentration in gas to be measured, and the pump-use composite ceramic layer 611 located on the thickness-direction one side DT1 (upper side in FIGS. 18 and 19) with respect to the detection-use composite ceramic layer 511 and used for adjusting oxygen concentration in gas to be measured in a measuring chamber SP. An insulation layer 570 is disposed between the detection-use composite ceramic layer 511 and the pump-use composite ceramic layer 611. A first conductor layer 550 is formed at the thickness-direction other side DT2 (lower side in FIGS. 18 and 19) of the detection-use composite ceramic layer 511, whereas a second conductor layer 555 is formed at the one side DT1 (upper side in FIGS. 18 and 19). Also, a first conductor layer 650 is formed at the one side DT1 of the pump-use composite ceramic layer 611, whereas a second conductor layer 655 is formed at the other side DT2. Furthermore, the heater layer 180 similar to that of the embodiment is laminated on the other side DT2 of the detection-use composite ceramic layer 511 and the first conductor layer 550, whereas a protection layer 560 is laminated on the one side DT1 of the pump-use composite ceramic layer 611 and the first conductor layer 650 (see FIGS. 18 and 19).

Figure 18:
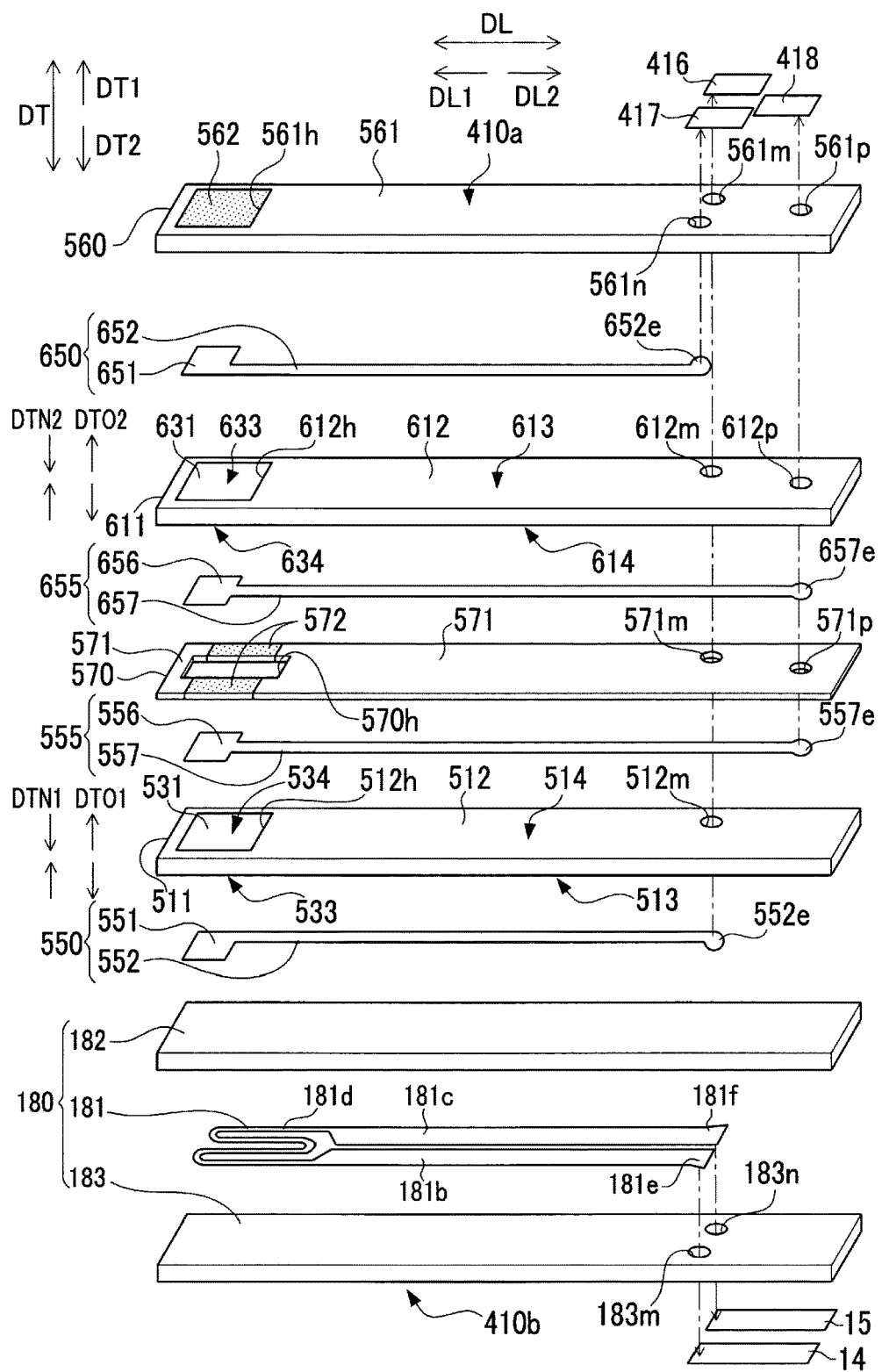
FIG. 18 is an exploded perspective view of the gas sensor element according to the modified embodiment.

The detection-use composite ceramic layer 511 includes a rectangular plate-like detection-use insulation portion 512 formed of alumina and having a through hole 512*h* which extends therethrough in the thickness direction DT and has a rectangular shape as viewed in plane, and a plate-like detection-use electrolyte portion 531 formed of zirconia ceramic and disposed within the through hole 512*h* of the detection-use insulation portion 512 (see FIG. 18). The detection-use insulation portion 512 has a first insulation main surface 513 facing the thickness-direction other side DT2, a second insulation main surface 514 facing the one side DT1, and a through-hole inner perimetric surface 515 which defines the through hole 512*h*. The detection-use electrolyte portion 531 has a first electrolyte main surface 533 facing the other side DT2, a second electrolyte main surface 534 facing the one side DT1, and an electrolyte outer perimetric surface 535 in close contact with the through-hole inner perimetric surface 515 of the detection-use insulation portion 512 (see FIGS. 20 and 21).

The first conductor layer 550 is composed of a rectangular first electrode layer 551 formed on the first electrolyte main surface 533 of the detection-use electrolyte portion 531 in such a manner as to be separated inward from the wall surface of the through hole 512*h* and a strip-like first extension layer 552 extending from the first electrode layer 551 toward the longitudinal-direction rear side DL2 (see FIG. 18). The first extension layer 552 extends in a continuous manner on the first electrolyte main surface 533 as well as on the first insulation main surface 513 (see FIG. 21). Similar to the first conductor layer 550, the second conductor layer 555 is composed of a rectangular second electrode layer 556 formed on the second electrolyte main surface 534 of the detection-use electrolyte portion 531 in such a manner as to be separated inward from the wall surface of the through hole 512*h* and a strip-like second extension layer 557 extending from the second electrode layer 556 toward the rear side DL2 (see FIG. 18). The second extension layer 557 extends in a continuous manner on the second electrolyte main surface 534 as well as on the second insulation main surface 514 (see FIG. 20).

Meanwhile, the pump-use composite ceramic layer 611, also, includes a rectangular pump-use insulation portion 612 formed of alumina and having a through hole 612*h* which extends therethrough in the thickness direction DT and has a rectangular shape as viewed in plane, and a plate-like pump-use electrolyte portion 631 formed of zirconia ceramic and disposed within the through hole 612*h* of the pump-use insulation portion 612 (see FIG. 18). The pump-use insulation portion 612 has a first insulation main surface 613 facing the thickness-direction one side DT1, a second insulation main surface 614 facing the thickness-direction other side DT2, and a through-hole inner perimetric surface 615 which defines the through hole 612h. The pump-use electrolyte portion 631 has a first electrolyte main surface 633 facing the one side DT1, a second electrolyte main surface 634 facing the other side DT2, and an electrolyte outer perimetric surface 635 in close contact with the through-hole inner perimetric surface 615 of the pump-use insulation portion 612 (see FIGS. 20 and 22).

The first conductor layer 650 is composed of a rectangular first electrode layer 651 formed on the first electrolyte main surface 633 of the pump-use electrolyte portion 631 in such a manner as to be separated inward from the wall surface of the through hole 612h and a strip-like first extension layer 652 extending from the first electrode layer 651 toward the rear side DL2 (see FIG. 18). The first extension layer 652 extends in a continuous manner on the first electrolyte main surface 633 as well as on the first insulation main surface 613 (see FIG. 22). Similar to the first conductor layer 650, the second conductor layer 655 is composed of a rectangular second electrode layer 656 formed on the second electrolyte main surface 634 of the pump-use electrolyte portion 631 in such a manner as to be separated inward from the wall surface of the through hole 612h and a strip-like second extension layer 657 extending from the second electrode layer 656 toward the rear side DL2 (see FIG. 18). The second extension layer 657 extends in a continuous manner on the second electrolyte main surface 634 as well as on the second insulation main surface 614 (see FIG. 20).

The insulation layer 570 has a rectangular through hole 570h extending therethrough in such a manner as to be aligned with the through holes 512h and 612h. The through hole 570h is surrounded by, in addition to the insulation layer 570, the detection-use composite ceramic layer 511 (detection-use electrolyte portion 531) and the pump-use composite ceramic layer 611 (pump-use electrolyte portion 631), thereby defining the hollow measuring chamber SP (see FIG. 19). The insulation layer 570 is composed of a body portion 571 formed of dense alumina, and two porous portions 572 and 572 which are formed of a porous ceramic and partially constitute two respective sides of the through hole 570h extending along the longitudinal direction DL and which are exposed sideward (direction orthogonal to the longitudinal direction DL and to the thickness direction DT) (see FIG. 18). The porous portions 572 are diffusion controlling layers for introducing gas to be measured into the measuring chamber SP from outside the gas sensor element 410 at a predetermined flow rate.

The protection layer 560 is laminated on the thickness-direction one side DT1 of the pump-use composite ceramic layer 611 and covers the first conductor layer 650. The protection layer 560 is composed of a porous portion 562 which covers the first electrode layer 651 and the pump-use electrolyte portion 631, and a protection portion 561 which is formed of a dense ceramic and overlies the pump-use insulation portion 612 to protect the same and in which a through hole 561h is formed and accommodates the porous portion 562 therein in a surrounding manner (see FIG. 18).

The aforementioned three sensor pads 416, 417, and 418 are formed on the protection portion 561. The sensor pad 416 electrically communicates with an end portion 552e of the first extension layer 552 located on the rear side DL2 through through holes 561m, 612m, 571m, and 512m. The sensor pad 417 electrically communicates with an end portion 652e of the first extension layer 652 located on the rear side DL2 through a through hole 561n (see FIG. 18).

Furthermore, the sensor pad 418 electrically communicates with an end portion 557e of the second extension layer 557 and with an end portion 657e of the second extension layer 657 through through holes 561p, 612p, and 571p (see FIG. 18).

In the gas sensor element 410 according to the present modified embodiment, oxygen is supplied beforehand into the porous first electrode layer 551 for use as reference gas. Under this condition, the direction and magnitude of current flowing between the first electrode layer 651 and the second electrode layer 656 between which the pump-use electrolyte portion 631 is sandwiched are adjusted such that the pump-use electrolyte portion 631 pumps out oxygen from the measuring chamber SP to the porous portion 562 or pumps oxygen into the measuring chamber SP from the porous portion 562 in order to establish a predetermined potential difference between the first electrode layer 551 and the second electrode layer 556 between which the detection-use electrolyte portion 531 is sandwiched (maintain the oxygen concentration within the measuring chamber SP at a fixed level). Notably, since the magnitude of current flowing between the first electrode layer 651 and the second electrode layer 656 corresponds to the oxygen concentration of gas to be measured which flows into the measuring chamber SP through the porous portions 572, the oxygen concentration of gas to be measured can be detected from the magnitude of current.

Figure 20:
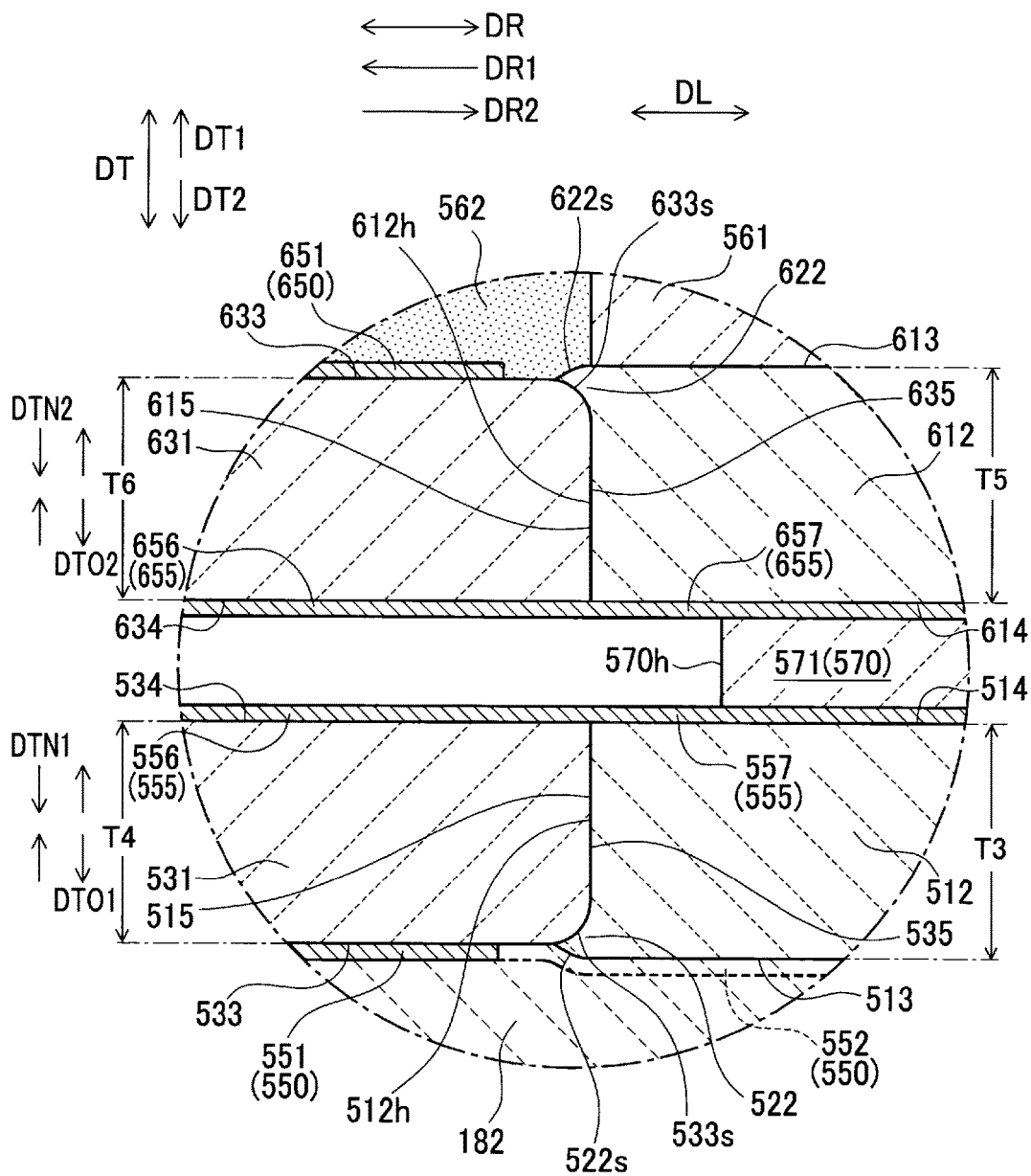
FIG. 20 is an enlarged sectional view (sectional view taken along line H-H of FIG. 17) of the gas sensor element according to the modified embodiment.
Figure 21:
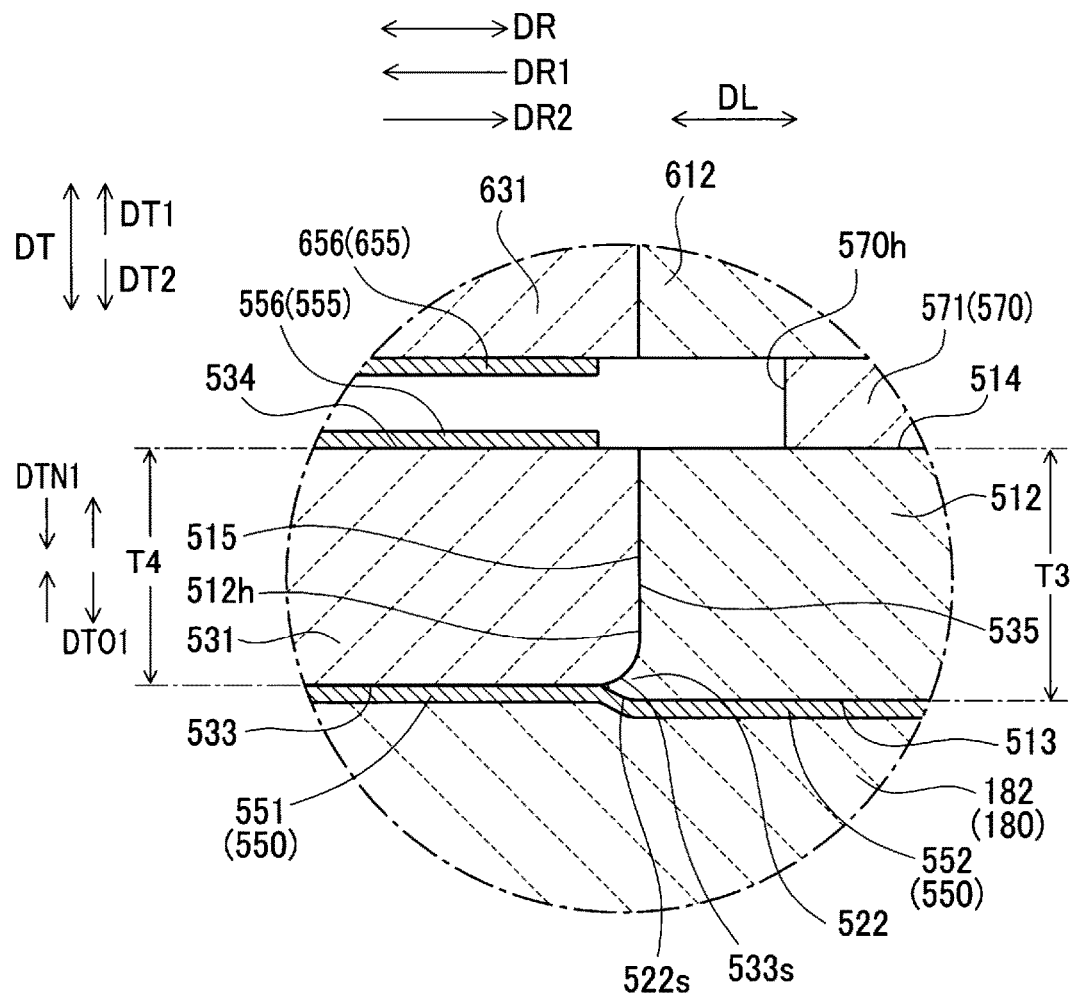
FIG. 21 is an enlarged sectional view (sectional view taken along line I-I of FIG. 17) of the gas sensor element according to the modified embodiment.

Next, in the gas sensor element 410 according to the present modified embodiment, the boundary and its periphery between the detection-use insulation portion 512 and the detection-use electrolyte portion 531 of the detection-use composite ceramic layer 511 will be described in detail. As shown in FIGS. 20 and 21, the thickness T4 (160 μm) of the detection-use electrolyte portion 531 is smaller than the thickness T3 (180 μm) of the detection-use insulation portion 512 (T4<T3). However, the second electrolyte main surface 534 of the detection-use electrolyte portion 531 is flush with the second insulation main surface 514 of the detection-use insulation portion 512. By contrast, the first electrolyte main surface 533 of the detection-use electrolyte portion 531 is located on the thickness-direction one side DT1 (thickness-direction inward side DTN1 of the detection-use composite ceramic layer 511 or upper side in FIGS. 20 and 21) with respect to the first insulation main surface 513 of the detection-use insulation portion 512.

The detection-use insulation portion 512 has, on a first insulation main surface 513 side, a protruding portion 522 overlying the first electrolyte main surface 533 of the detection-use electrolyte portion 531 and protruding toward the inward side DR1 of the through hole 512h. The protruding portion 522 has such a form as to reduce in thickness toward the inward side DR1 of the through hole 512h (as it progresses leftward in FIGS. 20 and 21); i.e., a tapering form. Notably, in the present modified embodiment, also, the protruding portion 522 is formed along the entire perimeter of the through hole 512h.

Furthermore, the first insulation main surface 513 of the detection-use insulation portion 512 has a form in which a protrusion surface 522s of the protruding portion 522 progresses toward the thickness-direction inward side DTN1 (herein, toward the thickness-direction one side DT1) and approaches the first electrolyte main surface 133 as it progresses toward the inward side DR1 of the through hole 512h. That is, the protrusion surface 522s of the protruding portion 522 is a gentle slope which progresses upward as it progresses leftward in FIGS. 20 and 21, and the level difference between the first insulation main surface 513 of the detection-use insulation portion 512 and the first electrolyte main surface 533 of the electrolyte portion 531 is mitigated at the protruding portion 522. Therefore, as shown in FIG. 21, the first extension layer 552 of the first conductor layer 550 gently extends in the longitudinal direction DL.

Figure 22:
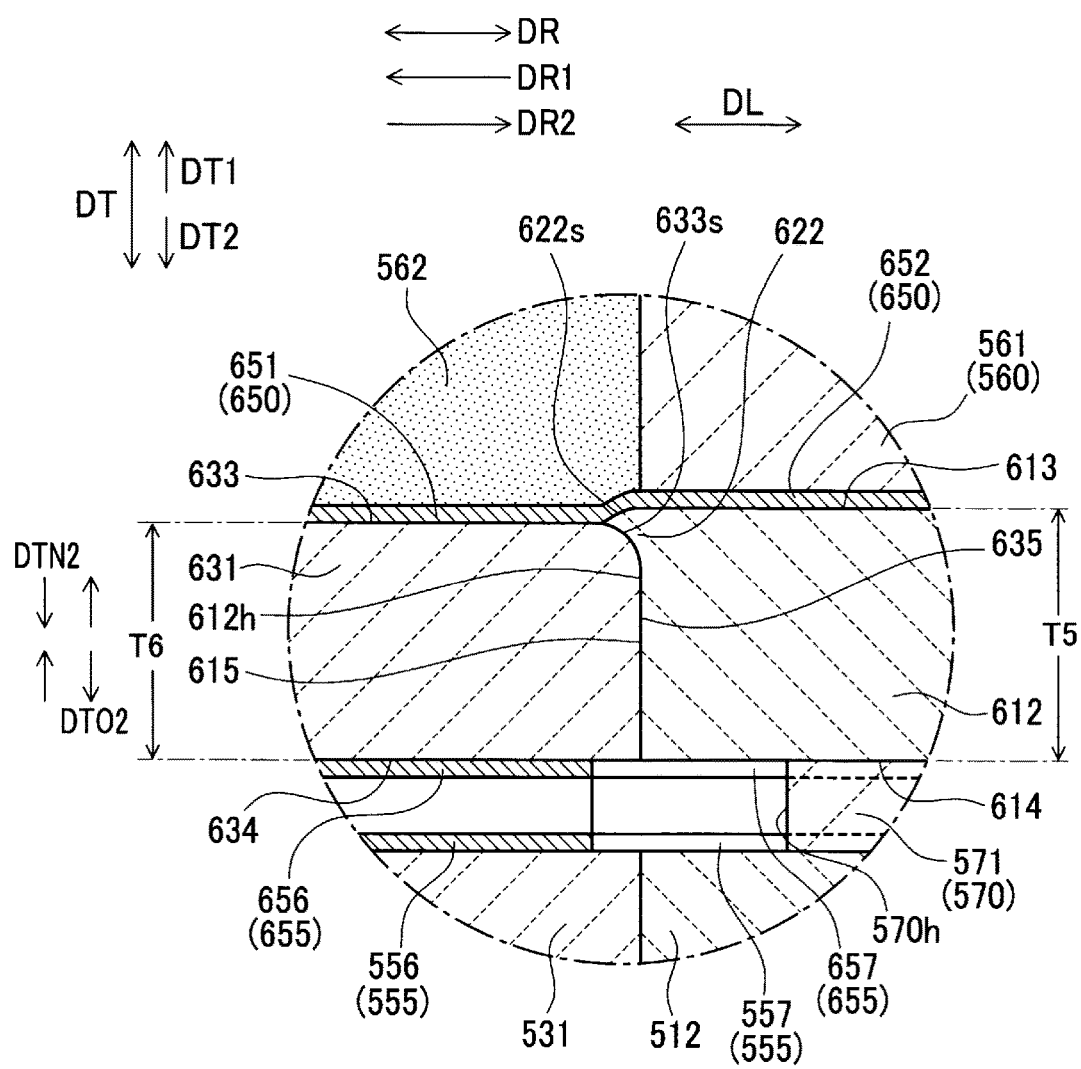
FIG. 22 is an enlarged sectional view (sectional view taken along line J-J of FIG. 17) of the gas sensor element according to the modified embodiment.

Next, the pump-use composite ceramic layer 611 will be discussed. As shown in FIGS. 20 and 22, in the pump-use composite ceramic layer 611, also, the thickness T6 (160 μm) of the pump-use electrolyte portion 631 is smaller than the thickness T5 (180 μM) of the pump-use insulation portion 612 (T6<T5). However, the second electrolyte main surface 634 of the pump-use electrolyte portion 631 is flush with the second insulation main surface 614 of the pump-use insulation portion 612. By contrast, the first electrolyte main surface 633 of the pump-use electrolyte portion 631 is located on the thickness-direction other side DT2 (thickness-direction inward side DTN2 of the pump-use composite ceramic layer 611 or lower side in FIGS. 20 and 22) with respect to the first insulation main surface 613 of the pump-use insulation portion 612.

The pump-use insulation portion 612 has, on a first insulation main surface 613 side, a protruding portion 622 overlying the first electrolyte main surface 633 of the pump-use electrolyte portion 631 and protruding toward the inward side DR1 of the through hole 612h. The protruding portion 622 has such a form as to reduce in thickness toward the inward side DR1 of the through hole 612h (as it progresses leftward in FIGS. 20 and 22); i.e., a tapering form. Notably, in the present modified embodiment, also, the protruding portion 622 is formed along the entire perimeter of the through hole 612h.

Furthermore, the first insulation main surface 613 of the pump-use insulation portion 612 has a form in which a protrusion surface 622s of the protruding portion 622 progresses toward the thickness-direction inward side DTN2 (herein, toward the thickness-direction other side DT2) and approaches the first electrolyte main surface 633 as it progresses toward the inward side DR1 of the through hole 612h. That is, the protrusion surface 622s is a gentle slope which progresses upward as it progresses leftward in FIGS. 20 and 22, and the level difference between the first insulation main surface 613 of the pump-use insulation portion 612 and the first electrolyte main surface 633 of the electrolyte portion 631 is mitigated at the protruding portion 622. Therefore, as shown in FIG. 22, the first extension layer 652 of the first conductor layer 650 gently extends in the longitudinal direction DL.

Thus, in the gas sensor element 410 according to the present modified embodiment, the first conductor layer 550 (first extension layer 552) extending in a continuous manner on the first electrolyte main surface 533 as well as on the first insulation main surface 513 is unlikely to suffer the occurrence of cracking or breaking. Furthermore, the first conductor layer 650 (first extension layer 652) extending in a continuous manner on the first electrolyte main surface 633 as well as on the first insulation main surface 613 is also unlikely to suffer the occurrence of cracking or breaking. Thus, the gas sensor element 410 can provide high reliability.

Furthermore, an overlying surface 533s of the first electrolyte main surface 533 of the detection-use electrolyte portion 531 which the protruding portion 522 overlies from the thickness-direction outward side DTO1 has such a form as to extend toward the outward side DR2 of the through hole 512h as well as toward the thickness-direction inward side DTN1 (herein, thickness-direction other side DT2). That is, the overlying surface 533s approaches the second electrolyte main surface 534; i.e., inclination thereof increases, as it progresses toward the outward side DR2 (see FIG. 21).

That is, in the detection-use composite ceramic layer 511 of the gas sensor element 410, the overlying surface 533s of the first electrolyte main surface 533 is deformed in the form of an arc, whereby the protruding portion 522 of the detection-use insulation portion 512 is in close contact with the overlying surface 533s of the detection-use electrolyte portion 531. Thus, an angular portion is not formed in a region of the detection-use electrolyte portion 531 which the protruding portion 522 overlies, whereby there can be restrained the occurrence of cracking in the protruding portion 522 starting from any portion of the overlying surface 533s.

Also, in the pump-use composite ceramic layer 611, an overlying surface 633s of the first electrolyte main surface 633 of the pump-use electrolyte portion 631 which the protruding portion 622 overlies from the thickness-direction outward side DTO2 has such a form as to extend toward the outward side DR2 of the through hole 612h as well as toward the thickness-direction inward side DTN2 (herein, thickness-direction other side DT2). That is, the overlying surface 633s approaches the second electrolyte main surface 634; i.e., inclination thereof increases, as it progresses toward the outward side DR2 (see FIG. 22).

Thus, in the pump-use composite ceramic layer 611 of the gas sensor element 410, also, the overlying surface 633s of the first electrolyte main surface 633 is deformed in the form of an arc, whereby the protruding portion 622 of the pump-use insulation portion 612 is in close contact with the overlying surface 633s of the pump-use electrolyte portion 631. Thus, an angular portion is not formed in a region of the pump-use electrolyte portion 631 which the protruding portion 622 overlies, whereby there can be restrained the occurrence of cracking in the protruding portion 622 starting from any portion of the overlying surface 633s.

Since the detection-use electrolyte portion 531 is formed by firing a green detection-use electrolyte portion 731 (which will be described herein later) formed of an electrolyte green sheet, the thickness T4 of the detection-use electrolyte portion 531 can be rendered uniform among products; thus, properties of an oxygen concentration cell (sensor cell) composed of the detection-use electrolyte portion 531, the first electrode layer 551, and the second electrode layer 556 can be rendered uniform among the gas sensor elements 410.

Furthermore, since the detection-use electrolyte portion 531 is thinner than the detection-use insulation portion 512 (T4<T3), although pressure is applied in the thickness direction DT in the course of manufacture, pressure is unlikely to be applied to the green detection-use electrolyte portion 731 which is to become the detection-use electrolyte portion 531; thus, variation is unlikely to arise in the thickness of the detection-use electrolyte portion 531. Therefore, variations in properties can be further reduced among the gas sensor elements 410.

Similar to the above-mentioned detection-use electrolyte portion 531, since the pump-use electrolyte portion 631 is formed by firing a green pump-use electrolyte portion 831 (which will be described herein later) formed of an electrolyte green sheet, the thickness T6 of the pump-use electrolyte portion 631 can be rendered uniform among products; thus, properties of an oxygen concentration cell (pump cell) composed of the electrolyte portion 631, the first electrode layer 651, and the second electrode layer 656 can be rendered uniform among the gas sensor elements 410.

Furthermore, since the pump-use electrolyte portion 631 is thinner than the pump-use insulation portion 612 (T6<T5), similar to the detection-use electrolyte portion 531, variations in the thickness of the pump-use electrolyte portion 631 caused by compression are unlikely to occur; thus, variations in properties can be further reduced among the gas sensor elements 410.

Figure 19:
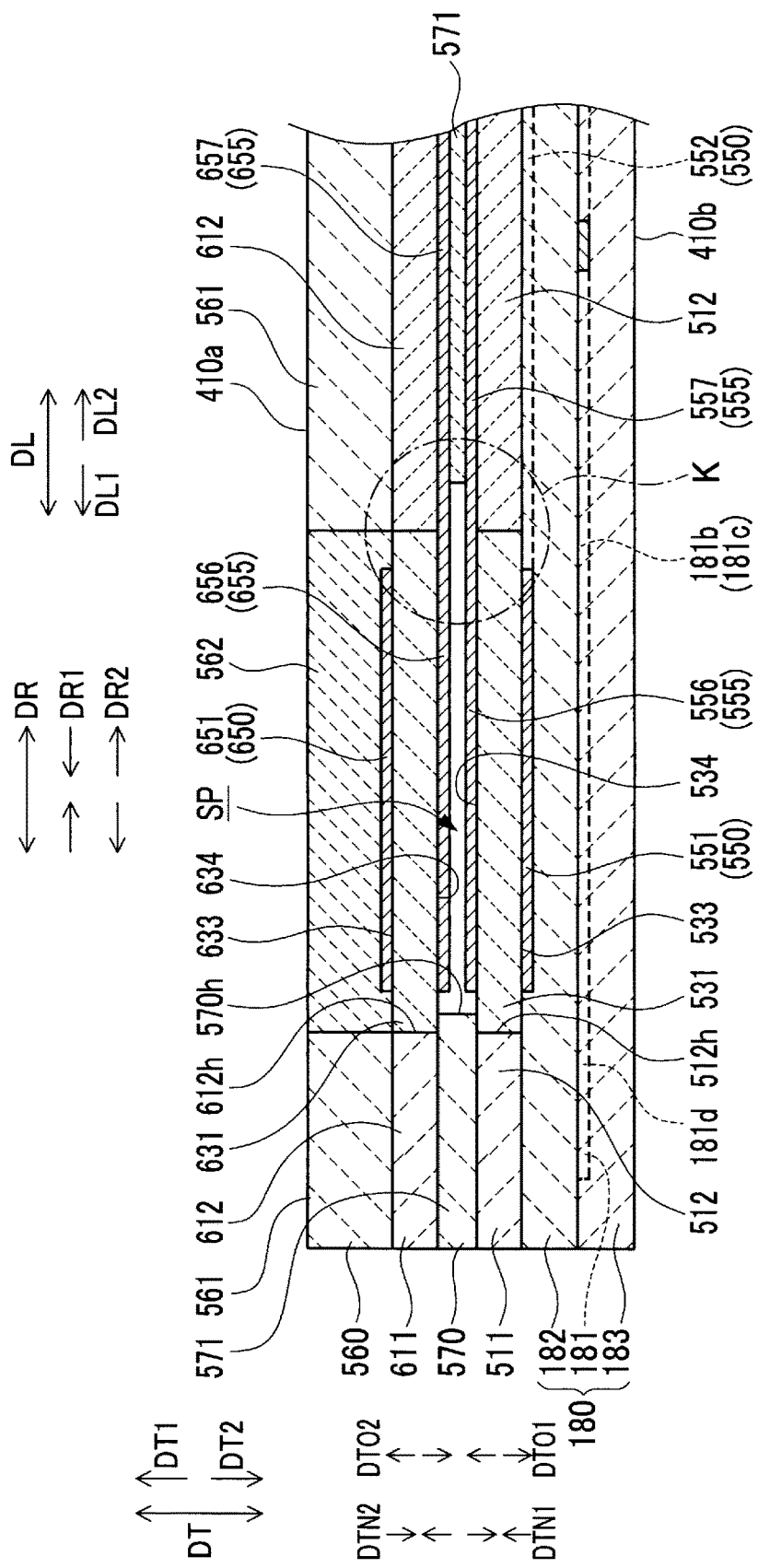
FIG. 19 is an enlarged sectional view (sectional view taken along line G-G of FIG. 17) showing the structure of the gas sensor element according to the modified embodiment.

Since the second electrolyte main surface 534 of the detection-use electrolyte portion 531 and the second insulation main surface 514 of the detection-use insulation portion 512 are flush with each other, the second conductor layer 555 (second extension layer 557) extending in a continuous manner on the second electrolyte main surface 534 as well as on the second insulation main surface 514 extends in the longitudinal direction DL without involvement of a level difference (see FIGS. 19 and 20). Similarly, since the second electrolyte main surface 634 of the pump-use electrolyte portion 631 and the second insulation main surface 614 of the pump-use insulation portion 612 are flush with each other, the second conductor layer 655 (second extension layer 657) extending in a continuous manner on the second electrolyte main surface 634 as well as on the second insulation main surface 614 extends in the longitudinal direction DL without involvement of a level difference (see FIGS. 19 and 20). Therefore, the second conductor layer 555 (second extension layer 557) and the second conductor layer 655 (second extension layer 657) are unlikely to suffer the occurrence of cracking or breaking, so that the gas sensor element 410 provides high reliability.

In the gas sensor element 410 of the present modified embodiment, the second electrode layer 556 is formed on the second electrolyte main surface 534 which is disposed flush with the second insulation main surface 514. Thus, in screen printing a green second electrode layer 756 (which will be described herein later) which is to become the second electrode layer 556 by firing, the thickness of the green second electrode layer 756 can be readily controlled. Thus, among the gas sensor elements 410 in which reference gas is in contact with the first electrode layer 551, whereas gas to be measured within the measuring chamber SP is in contact with the second electrode layer 556, variations in properties of the oxygen concentration cell can be suppressed, whereby properties of the oxygen concentration cell can be rendered uniform.

Additionally, the second electrode layer 656, also, is formed on the second electrolyte main surface 634 which is disposed flush with the second insulation main surface 614. Thus, in screen printing a green second electrode layer 856 (which will be described herein later) which is to become the second electrode layer 656 by firing, the thickness of the green second electrode layer 856 can be readily controlled. Thus, among the gas sensor elements 410 in which gas to be measured within the measuring chamber SP is in contact with the second electrode layer 656, variations in properties of the pump cell can be suppressed, whereby properties of the pump cell can be rendered uniform.

Also, because of employment of the above-mentioned gas sensor element 410, the gas sensor 401 according to the present modified embodiment is unlikely to suffer the occurrence of cracking or breaking of the first conductor layers 550 and 650 (first extension layers 552 and 652) and thus provides high reliability.

Next, a method of manufacturing the gas sensor 401 according to the present modified embodiment will be described with reference to the drawings. Two green insulation-portion sheets 212s and 212s (insulation green sheets) having a thickness of 230 μm and two green electrolyte-portion sheets 231s and 231s (electrolyte green sheets) having a smaller thickness of 200 μm, are prepared beforehand by the doctor blade process.

Next, similar to the embodiment, sheet through holes 712h and 812h are formed in the respective green insulation-portion sheets 212s and 212s in such a manner as to extend therethrough in the sheet thickness direction ST (through hole forming step, see FIG. 7).

The green detection-use insulation portion 712 and the green pump-use insulation portion 812 have the respective first insulation sheet main surfaces 713 and 813 facing the sheet thickness-direction other side ST2, the respective second insulation sheet main surfaces 714 and 814 facing the sheet thickness-direction one side ST1, and the respective sheet through-hole inner perimetric surfaces 715 and 815, which are the inner perimetric surfaces of the sheet through holes 712h and 812h (see FIG. 8).

Notably, similar to the embodiment, the sheet through holes 712h and 812h have such a form as to taper toward the thickness-direction other side DT2 (see FIGS. 8 and 9).

Subsequently, an inserting step is performed for inserting the green electrolyte portions 731 and 831 into the sheet through holes 712h and 812h of the green insulation portions 712 and 812, respectively.

Figure 10A:
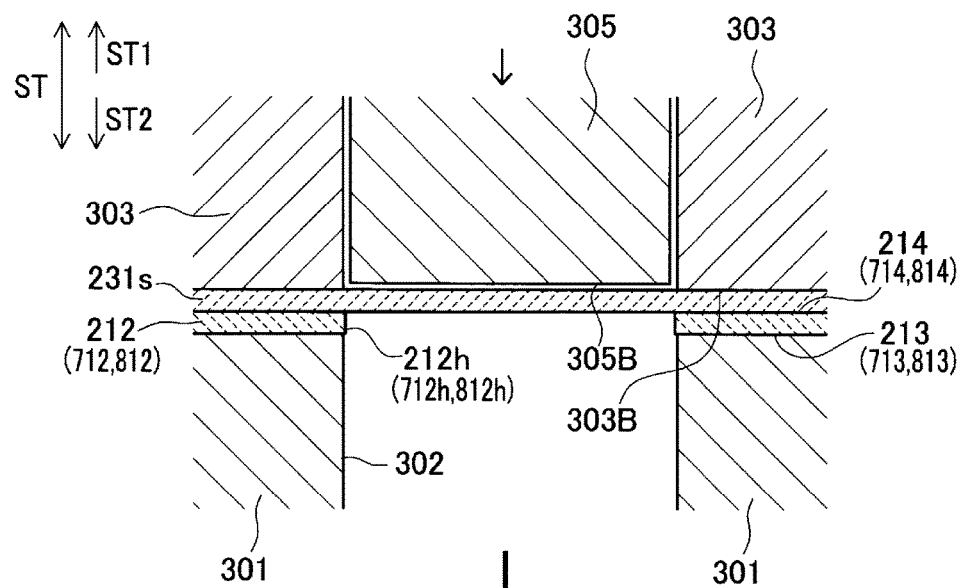
FIGS. 10A and 10B are explanatory views showing an inserting step in the method of manufacturing a gas sensor element according to the embodiment and the modified embodiment.
Figure 10B:
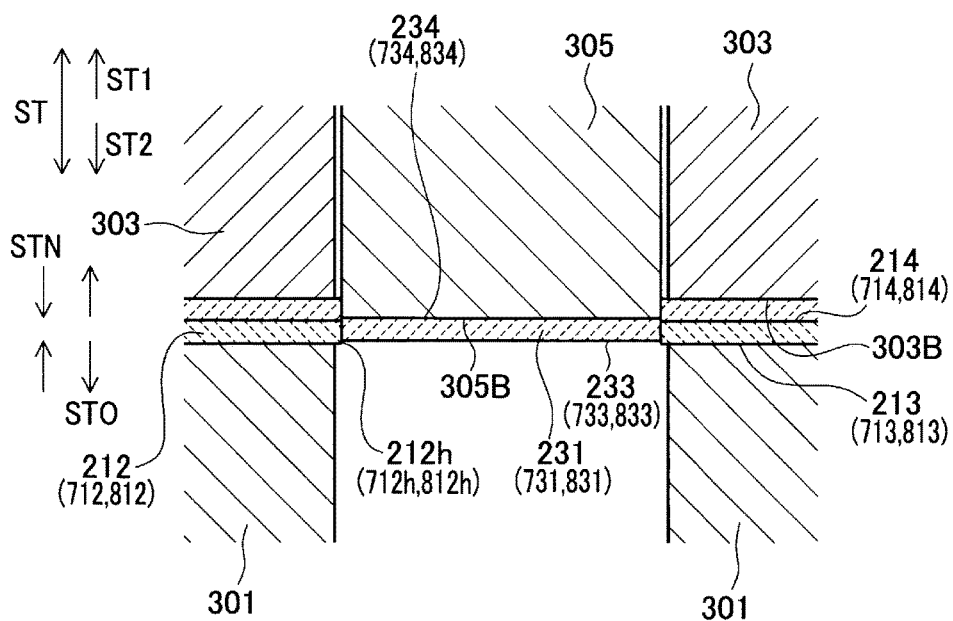

Similar to the embodiment, the green insulation portion 712 (812) and the green electrolyte-portion sheet 231s are held between the lower die 301 and the upper die 303; then, by use of the punch 305, the green electrolyte portion 731 (831) is punched out from the green electrolyte-portion sheet 231s and inserted into the sheet through hole 712h (812h) of the green insulation portion 712 (812) (see FIG. 10A and FIG. 10B). By this procedure, the green electrolyte portion 731 (831) is disposed in such a manner that a second electrolyte sheet main surface 734 (843) of the green electrolyte portion 731 (831) facing the one side ST1 (upper side in FIG. 10A and FIG. 10B) is located (protrudes) on the one side ST1 (sheet thickness-direction outward side STO) with respect to the second insulation sheet main surface 714 (814) of the green insulation portion 712 (812), while a first electrolyte sheet main surface 733 (833) facing the other side DT2 is located on the one side ST1 (sheet thickness-direction inward side STN) with respect to the first insulation sheet main surface 713 (813) of the green insulation portion 712 (812) (see FIG. 10B).

Next, a compressing step is performed. The compressing step compresses the green insulation portions 712 and 812 in the sheet thickness-direction ST, thereby forming green composite layers 711 and 811 composed of the green insulation portions 712 and 812 and the green electrolyte portions 731 and 831 inserted in the sheet through holes 712h and 812h, respectively.

Notably, the compressing step is performed in a manner similar to that of the embodiment by use of the aforementioned first compression die 311 and second compression die 316 (see FIG. 11).

Thus, similar to the green composite layer 211 of the embodiment, the green composite layers 711 and 811 are such that the second insulation sheet main surfaces 714 and 814 of the green insulation portions 712 and 812 facing the one side ST1 and the second electrolyte sheet main surfaces 734 and 834 of the green electrolyte portions 731 and 831 facing the one side ST1, respectively, become flush with each other (see FIGS. 12 and 13). By contrast, the first electrolyte sheet main surfaces 733 and 833 of the green electrolyte portions 731 and 831, respectively, are located on the sheet thickness-direction inward side STN (sheet thickness-direction one side ST1) with respect to the first insulation sheet main surfaces 713 and 813 of the green insulation portions 712 and 812; i.e., within the sheet through holes 712h and 812h.

Specifically, the corner portion C1 of the green insulation portion 712 (812) located on the first insulation sheet main surface 713 (813) side and defined by the sheet through-hole inner perimetric surface 715 (815) and the first insulation sheet main surface 713 (813) is deformed by compression in such a manner as to overlie the first electrolyte sheet main surface 733 (833) of the green electrolyte portion 731 (831), thereby becoming a green protruding portion 722 (822) which protrudes toward the inward side DR1 (leftward side in FIG. 13) of the sheet through hole 712h (812h) and reduces in thickness toward the inward side DR1. Furthermore, in association with deformation of the corner portion C1, a corner portion C2 of the green electrolyte portion 731 (831) which is defined by an electrolyte sheet outer perimetric surface 735 (835) and the first electrolyte sheet main surface 733 (833) is also deformed in such a manner that an overlying surface 733s (833s) of the first electrolyte sheet main surface 733 (833) which the green protruding portion 722 (822) overlies from the outward side STO (the other side ST2) has such a form as to extend toward the outward side DR2 of the sheet through hole 712h (812h) as well as toward the sheet thickness-direction inward side STN (herein, the sheet thickness-direction one side ST1). In the present embodiment, the corner portion C2 is deformed in such a manner as to be rounded to a quarter of a circle convexed outward.

Figure 14:
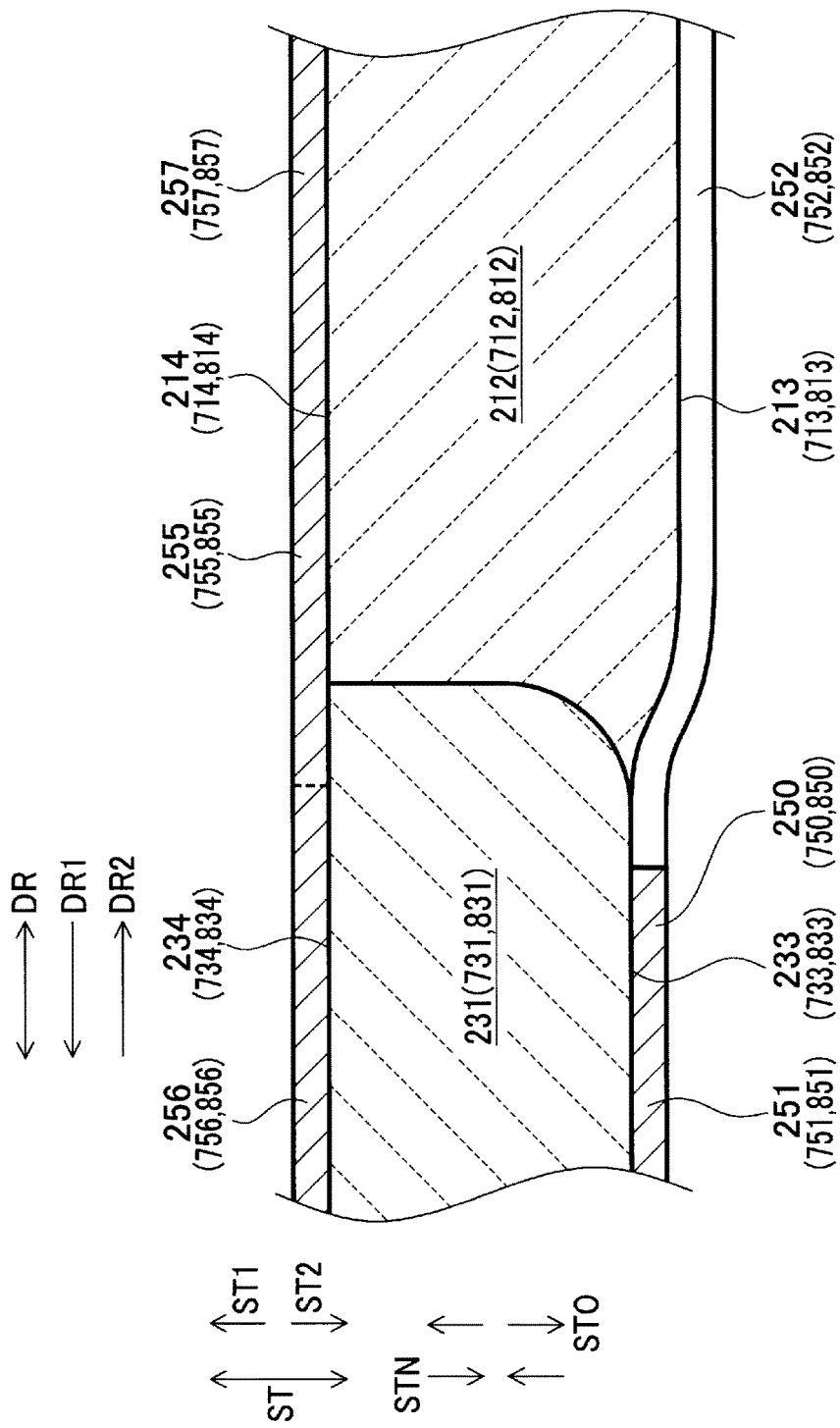
FIG. 14 is an explantory view showing a first printing step and a second printing step in the method of manufacturing a gas sensor element according to the embodiment and the modified embodiment.

Next, in the first printing step, a green first conductor layer 750 (850) (a green first electrode layer 751 (851) and a green first extension layer 752 (852)) is formed by screen printing in such a manner as to extend in a continuous manner on the first electrolyte sheet main surface 733 (833) as well as on the first insulation sheet main surface 713 (813) (see FIG. 14).

Subsequently, in the second printing step, a green second conductor layer 755 (855) (a green second electrode layer 756 (856) and a green second extension layer 757 (857)) is formed by screen printing in such a manner as to extend in a continuous manner on the second electrolyte sheet main surface 734 (834) as well as on the second insulation sheet main surface 714 (814) (see FIG. 14).

Figure 23:
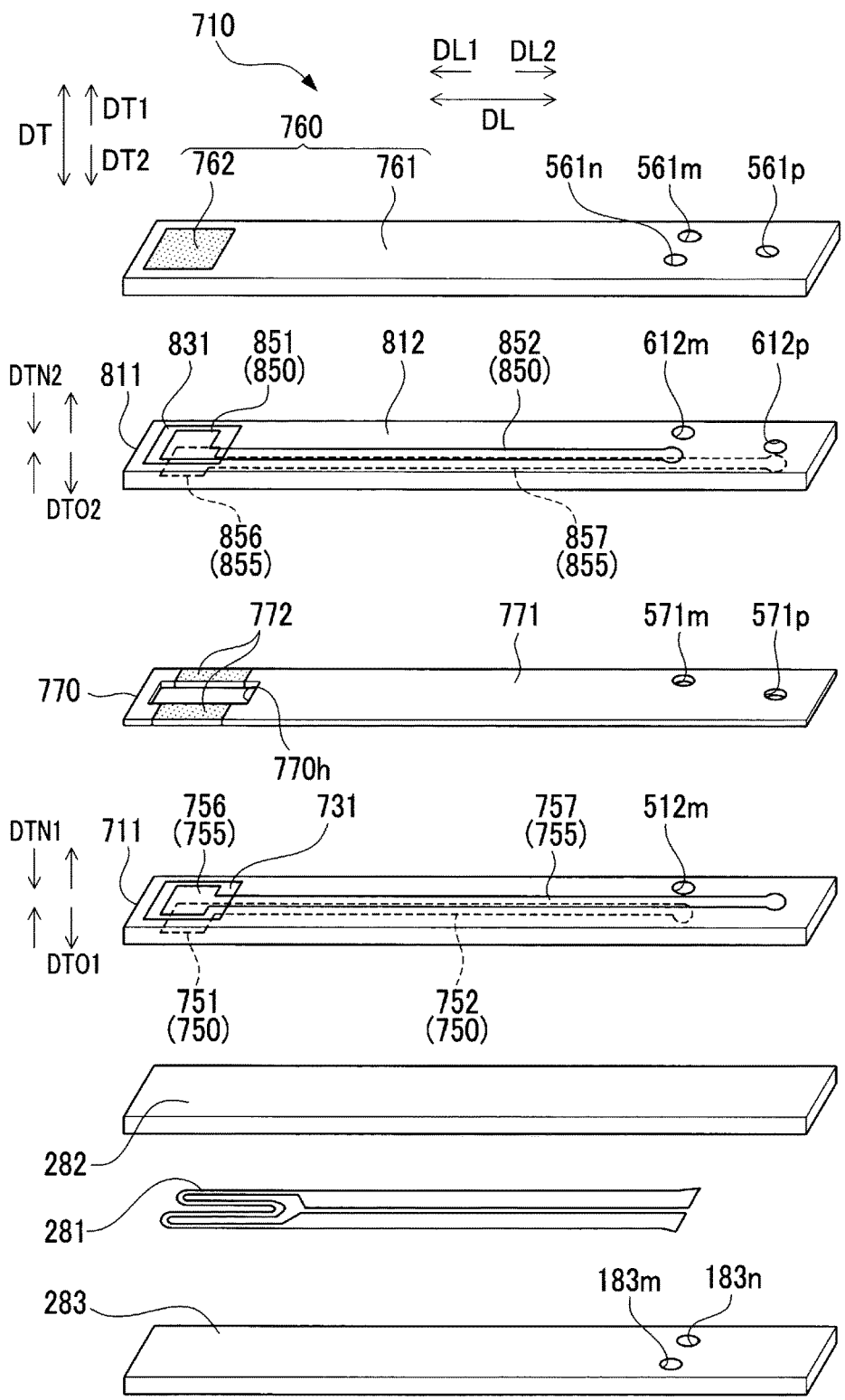
FIG. 23 is an explanatory view for explaining a method of manufacturing a gas sensor element according to the modified embodiment.

Next, as shown in FIG. 23, the green insulation layers 283 and 282, the green detection-use composite layer 711, a green insulation layer 770, the green pump-use composite layer 811, and a green protection layer 760 are sequentially laminated together, thereby forming a green laminate 710. Notably, in lamination, the green pump-use composite layer 811, and the green first conductor layer 850 and the green second conductor layer 855 which are formed on the green pump-use composite layer 811 are laminated in a vertically inverted manner (see FIGS. 19 to 23). Similar to the embodiment, the green heater pattern 281 and the through holes 183m and 183n are formed beforehand on and in the green insulation layer 283. The green insulation layer 770 is composed of a green body portion 771 which is to become the dense body portion 571 by firing, and a green porous portion 772 which is to become the porous portion 572 by firing, and has a rectangular through hole 770h. The green porous portion 772 partially constitutes two sides of the through hole 770h extending along the longitudinal direction DL, and is exposed sideward (direction orthogonal to the longitudinal direction DL and to the thickness direction DT). The green protection layer 760 is composed of a green porous portion 762 which is to become the porous portion 562 after firing, and a green protection portion 761 which surrounds the green porous portion 762 and is to become the protection portion 561 after firing. The through holes 561m, 561n, and 561p which extend through the green protection portion 761 and are connected to the through holes 612m and 612p and the green first conductor layer 850, respectively, are formed beforehand at the rear side DL2 of the green protection layer 760. Also, green pads (not shown) which are to become the heater pads 14 and 15 and the sensor pads 416, 417, and 418 after firing are printed on the green laminate 710.

Next, a firing step for firing the green laminate 710 (see FIG. 23) is performed, thereby forming the gas sensor element 410 which includes the detection-use composite ceramic layer 511, the first conductor layer 550 and the second conductor layer 555, the pump-use composite ceramic layer 611, and the first conductor layer 650 and the second conductor layer 655 (see FIG. 17).

In the method of manufacturing the gas sensor element 410 according to the present modified embodiment, also, the compressing step compresses the green insulation portions 712 and 812 in the sheet thickness direction ST to shrink the sheet through holes 712h and 812h, respectively. By this procedure, the sheet through-hole inner perimetric surfaces 715 and 815 are brought in close contact with the electrolyte sheet outer perimetric surfaces 735 and 835 of the green electrolyte portions 731 and 831, respectively.

Furthermore, by means of forming the green protruding portions 722 and 822, the composite ceramic layers 511 and 611 after firing can readily have the protruding portions 522 and 622, respectively.

Thus, there can be manufactured the highly reliable gas sensor element 410 in which the first conductor layers 550 and 650 formed by firing the green first conductor layers 750 and 850, respectively, are unlikely suffer the occurrence of cracking or breaking.

According to this manufacturing method, the compressing step forms the green overlying surfaces 733s and 833s of the first electrolyte sheet main surfaces 733 and 833 of the green electrolyte portions 731 and 831, respectively, into such a form as to extend toward the outward side DR2 of the sheet through holes 712h and 812h as well as toward the sheet thickness-direction inward side STN. Thus, in the composite ceramic layers 511 and 611 after firing, there can be appropriately restrained the occurrence of cracking in the protruding portions 522 and 622 starting from any portions of the overlying surfaces 533s and 633s, respectively.

The inserting step inserts the green electrolyte portions 731 and 831 into the sheet through holes 712h and 812h, respectively, in such a manner that the green electrolyte portions 731 and 831 protrude toward the outward side STO (one side ST1) with respect to the second insulation sheet main surfaces 714 and 814 of the green insulation portions 712 and 812 (see FIG. 10B). Thus, in the compressing step, by means of pressing with the flat second compression surface 317 of the second compression die 316, the second electrolyte sheet main surfaces 734 and 834 of the green electrolyte portions 731 and 831 can be readily rendered flush with the second insulation sheet main surfaces 714 and 814 of the green insulation portions 712 and 812, respectively. Thus, there can be easily formed the gas sensor element 410 having the composite ceramic layers 511 and 611 in which the second electrolyte main surfaces 534 and 634 of the electrolyte portions 531 and 631 are flush with the second insulation main surfaces 514 and 614 of the insulation portions 512 and 612, respectively.

By virtue of this, there can be manufactured the gas sensor element 410 having higher reliability in which the second conductor layers 555 and 655 formed by firing the green second conductor layers 755 and 855, also, are unlikely to suffer the occurrence of cracking or breaking at a portion on the boundary between the two main surfaces.

Furthermore, since the second electrolyte sheet main surfaces 734 and 834 are flush with the second insulation sheet main surfaces 714 and 814, respectively, the thicknesses of the green second conductor layers 755 and 855 formed by screen printing, and, in turn, the thicknesses of the second conductor layers 555 and 655 (particularly, the thicknesses of the second electrode layers 556 and 656 on the second electrolyte main surfaces 534 and 634) after firing can be easily controlled.

While the present invention has been described with reference to the embodiment and the modified embodiment, the present invention is not limited thereto, but may be modified as appropriate without departing from the gist of the invention.

DESCRIPTION OF REFERENCE NUMERALS

1, 401: gas sensor
10, 410: gas sensor element
78, 79, 478, 479: lead
111, 511, 611: composite ceramic layer
112, 512, 612: insulation portion
112h: through hole (of insulation portion)
113, 513, 613: first insulation main surface
114, 514, 614: second insulation main surface
115, 515, 615: through-hole inner perimetric surface
121, 521, 621: through-hole inner perimetric portion
122, 522, 622: protruding portion
122s, 522s, 622s: protruding surface (of protruding portion)
131, 531, 631: electrolyte portion
133, 533, 633: first electrolyte main surface
133s, 533s, 633s: overlying surface (of first electrolyte main surface)
134, 534, 634: second electrolyte main surface
135, 535, 635: electrolyte outer perimetric surface
150, 550, 650: first conductor layer
151, 551, 651: first electrode layer
152, 552, 652: first extension layer
155, 555, 655: second conductor layer
156, 556, 656: second electrode layer
157, 557, 657: second extension layer
152e, 157e, 552e, 557e, 652e, 657e: end portion (of extension layer)
161: protection portion (gas introduction path formation member)
161h: through hole (of protection portion) (gas introduction path)
162: porous portion (gas introduction path formation member)
170: introduction path formation layer (ambient-atmosphere introduction path formation member)
175: atmosphere introduction groove (ambient-atmosphere introduction path)
182: insulation layer (ambient-atmosphere introduction path formation member)
211: green composite layer (green composite ceramic layer)
212: green insulation portion
212h, 712h, 812h: sheet through hole
212s: green insulation-portion sheet (insulation green sheet)
213: first insulation sheet main surface
214: second insulation sheet main surface
215, 715, 815: sheet through-hole inner perimetric surface
222, 722, 822: green protruding portion
222s, 722s, 822s: green protrusion surface (of green protruding portion)
231, 731, 831: green electrolyte portion
231s: green electrolyte-portion sheet (electrolyte green sheet)
233, 733, 833: first electrolyte sheet main surface
233s, 733s, 833s: green overlying surface
234: second electrolyte sheet main surface
235, 735, 835: electrolyte sheet outer perimetric surface
250: green first conductor layer
251: green first electrode layer
252: green first extension layer
255: green second conductor layer
256: green second electrode layer
257: green second extension layer
311: first compression die
312: rubber plate member
313: first compression surface
***315: body member
316: second compression die
317: second compression surface
511: detection-use composite ceramic layer (composite ceramic layer)
512: detection-use insulation portion (insulation portion)
512h: through hole (of detection-use insulation portion)
513: first insulation main surface (of detection-use insulation portion)
514: second insulation main surface (of detection-use insulation portion)
531: detection-use electrolyte portion (electrolyte portion)
533: first electrolyte main surface (of detection-use electrolyte portion)
534: second electrolyte main surface (of detection-use electrolyte portion)
550: first conductor layer (of detection-use composite layer)
551: first electrode layer (of detection-use composite layer)
552: first extension layer (of detection-use composite layer)
555: second conductor layer (of detection-use composite layer)
556: second electrode layer (of detection-use composite layer)
557: second extension layer (of detection-use composite layer)
611: pump-use composite ceramic layer (composite ceramic layer)
612: pump-use insulation portion (insulation portion)
612h: through hole (of pump-use insulation portion)
613: first insulation main surface (of pump-use insulation portion)
614: second insulation main surface (of pump-use insulation portion)
631: pump-use electrolyte portion (electrolyte portion)
633: first electrolyte main surface (of pump-use electrolyte portion)
634: second electrolyte main surface (of pump-use electrolyte portion)
650: first conductor layer (of pump-use composite layer)
651: first electrode layer (of pump-use composite layer)
652: first extension layer (of pump-use composite layer)
655: second conductor layer (of pump-use composite layer)
656: second electrode layer (of pump-use composite layer)
657: second extension layer (of pump-use composite layer)
711: green detection-use composite layer (green composite ceramic layer)
712: green detection-use insulation portion (of green detection-use composite layer) (green insulation portion)

713: first insulation sheet main surface (of green detection-use insulation portion)
714: second insulation sheet main surface (of green detection-use insulation portion)
731: green detection-use electrolyte portion (of green detection-use composite layer) (green electrolyte portion)
733: first electrolyte sheet main surface (of green detection-use electrolyte portion)
734: second electrolyte sheet main surface (of green detection-use electrolyte portion)
750: green first conductor layer (of green detection-use composite layer)
751: green first electrode layer (of green detection-use composite layer)
752: green first extension layer (of green detection-use composite layer)
755: green second conductor layer (of green detection-use composite layer)
756: green second electrode layer (of green detection-use composite layer)
757: green second extension layer (of green detection-use composite layer)
811: green pump-use composite layer (green composite ceramic layer)
812: green pump-use insulation portion (of green pump-use composite layer) (green insulation portion)
813: first insulation sheet main surface (of green pump-use insulation portion)
814: second insulation sheet main surface (of green pump-use insulation portion) 831: green pump-use electrolyte portion (of green pump-use composite layer) (green electrolyte portion)
831: green pump-use electrolyte portion (of green pump-use composite layer) (green electrolyte portion)
833: (first electrolyte sheet main surface (of green pump-use electrolyte portion)
834: second electrolyte sheet main surface (of green pump-use electrolyte portion)
850: green first conductor layer (of green pump-use composite layer)
851: green first electrode layer (of green pump-use composite layer)
852: green first extension layer (of green pump-use composite layer)
855: green second conductor layer (of green pump-use composite layer)
856: green second electrode layer (of green pump-use composite layer)
857: green second extension layer (of green pump-use composite layer)
DT: thickness direction (of gas sensor element)
DT1: thickness-direction one side
DT2: thickness-direction other side
DTN, DTN1, DTN2: thickness-direction inward side (of composite ceramic layer)
DTO, DTO1, DTO2: thickness-direction outward side (of composite ceramic layer)
DR1: inward side (of through hole)
DR2: outward side (of through hole)
ST: sheet thickness direction (of green insulation portion)
ST1: sheet thickness-direction one side
ST2: sheet thickness-direction other side
STN: thickness-direction inward side (of green composite ceramic layer)
STO: thickness-direction outward side (of green composite ceramic layer)
AD: atmosphere introduction path (ambient-atmosphere introduction path)
GD: gas introduction path
KS: reference chamber
T1, T2, T3, T4, T5, T6: thickness
T1: thickness (of insulation portion)
T2: thickness (electrolyte portion)
T3, T5: thickness (of green insulation portion)
T4, T6: thickness (of green electrolyte portion)
TR: atmosphere flow path

The invention claimed is:

1. A gas sensor element comprising
a composite ceramic layer having a plate-like insulation portion formed of an insulating ceramic and having a through hole extending therethrough in a thickness direction and a plate-like electrolyte portion formed of a solid electrolyte ceramic and disposed within the through hole, and
a first conductor layer extending in a continuous manner on a first insulation main surface of the insulation portion intersecting with the thickness direction as well as on a first electrolyte main surface of the electrolyte portion intersecting with the thickness direction,
wherein the electrolyte portion has a thickness smaller than that of the insulation portion;
the first electrolyte main surface of the electrolyte portion is located on a thickness-direction inward side with respect to the first insulation main surface of the insulation portion;
the insulation portion has, on a first insulation main surface side, a protruding portion overlying and contacting the first electrolyte main surface of the electrolyte portion and protruding toward an inward side of the through hole in a direction intersecting with the thickness-direction;
the protruding portion has a tapering form in which its thickness reduces toward the inward side of the through hole in the direction intersecting with the thickness-direction and in which a protrusion surface of the protruding portion located on a thickness-direction outward side extends toward the inward side of the through hole in the direction intersecting with the thickness-direction as well as toward the thickness-direction inward side so as to form a slope; and
the first conductor layer extends in a continuous manner on the protrusion surface as well as on the first electrolyte main surface.

2. A gas sensor element as claimed in claim 1, wherein an overlying surface of the first electrolyte main surface which the protruding portion overlies from the thickness-direction outward side has such a form as to extend toward the outward side of the through hole as well as toward the thickness-direction inward side.

3. A gas sensor element as claimed in claim 1, wherein the electrolyte portion is formed by firing an electrolyte green sheet which contains the solid electrolyte ceramic.

4. A gas sensor element as claimed in claim 1, further comprising
a second conductor layer extending in a continuous manner on a second insulation main surface of the insulation portion located opposite the first insulation main surface as well as on a second electrolyte main surface of the electrolyte portion located opposite the first electrolyte main surface,
wherein the second insulation main surface and the second electrolyte main surface are flush with each other.

5. A gas sensor element as claimed in claim 4, wherein
the first conductor layer includes a first electrode layer formed on the first electrolyte main surface;
the second conductor layer includes a second electrode layer formed on the second electrolyte main surface;
the second conductor layer is formed by screen-printing electrode paste, followed by firing; and
the gas sensor element is configured such that, during use, reference gas is in contact with the first electrode layer, whereas gas to be measured is in contact with the second electrode layer.

6. A gas sensor element as claimed in claim 4, further comprising
an ambient-atmosphere introduction path formation member which defines an ambient-atmosphere introduction path for introducing ambient atmosphere to the first electrode layer, and
a gas introduction path formation member which defines a gas introduction path for introducing gas to be measured to the second electrode layer.

7. A gas sensor comprising a gas sensor element as claimed in claim 1.

8. A method of manufacturing the gas sensor element as claimed in claim 1, the gas sensor element comprising
a composite ceramic layer having a plate-like insulation portion formed of an insulating ceramic and having a through hole extending therethrough in a thickness direction, and a plate-like electrolyte portion formed of a solid electrolyte ceramic and disposed within the through hole, and
a first conductor layer extending in a continuous manner on a first insulation main surface of the insulation portion intersecting with the thickness direction as well as on a first electrolyte main surface of the electrolyte portion intersecting with the thickness direction,
wherein the electrolyte portion has a thickness smaller than that of the insulation portion;
the first electrolyte main surface of the electrolyte portion is located on a thickness-direction inward side with respect to the first insulation main surface of the insulation portion;
the insulation portion has, on a first insulation main surface side, a protruding portion overlying and contacting the first electrolyte main surface of the electrolyte portion and protruding toward an inward side of the through hole in a direction intersecting with the thickness-direction;
the protruding portion has a tapering form in which its thickness reduces toward the inward side of the through hole in the direction intersecting with the thickness-direction and in which a protrusion surface of the protruding portion located on a thickness-direction outward side extends toward the inward side of the through hole in the direction intersecting with the thickness-direction as well as toward the thickness-direction inward side so as to form a slope; and
the first conductor layer extends in a continuous manner on the protrusion surface as well as on the first electrolyte main surface,
the method comprising
an inserting step of inserting a plate-like green electrolyte portion formed of the solid electrolyte ceramic and being thinner than a plate-like green insulation portion containing the insulating ceramic and having a sheet through hole extending therethrough in a sheet thickness direction, into the sheet through hole in such a manner that the first electrolyte sheet main surface is located on a sheet thickness-direction inward side with respect to a first insulation sheet main surface of the green insulation portion;
a compressing step of pressing the first insulation sheet main surface of the green insulation portion to compress the green insulation portion in the sheet thickness direction;
a first printing step of forming a green first conductor layer which extends in a continuous manner on the first insulation sheet main surface of the green insulation portion as well as on the first electrolyte sheet main surface of the green electrolyte portion; and
a firing step of firing the green insulation portion, the green electrolyte portion, and the green first conductor layer to form the composite ceramic layer having the insulation portion and the electrolyte portion, and the first conductor layer;
wherein the compressing step forms a green protruding portion at a first insulation sheet main surface side of the green insulation portion in such a manner as to overlie the first electrolyte sheet main surface of the green electrolyte portion, to protrude toward an inward side of the sheet through hole, and to reduce in thickness toward the inward side.

9. A method of manufacturing a gas sensor element as claimed in claim 8, wherein
the gas sensor element is such that an overlying surface of the first electrolyte main surface which the protruding portion overlies from the thickness-direction outward side has such a form as to extend toward the outward side of the through hole as well as toward the thickness-direction inward side and
the compressing step forms a green overlying surface of the first electrolyte sheet main surface which the green protruding portion overlies from a sheet thickness-direction outward side, into such a form as to extend toward the outward side of the sheet through hole as well as toward a sheet thickness-direction inward side.

10. A method of manufacturing a gas sensor element as claimed in claim 8, wherein
the gas sensor element further comprises a second conductor layer extending in a continuous manner on a second insulation main surface of the insulation portion located opposite the first insulation main surface as well as on a second electrolyte main surface of the electrolyte portion located opposite the first electrolyte main surface;
the second insulation main surface and the second electrolyte main surface are flush with each other;
the inserting step inserts the green electrolyte portion in such a manner that a side of the green electrolyte portion corresponding to a second insulation sheet main surface located opposite the first insulation sheet main surface protrudes from the sheet through hole of the green insulation portion; and
the compressing step performs compression in such a manner that the second insulation sheet main surface of the green insulation portion and a second electrolyte sheet main surface of the green electrolyte portion located opposite the first electrolyte sheet main surface become flush with each other;
the method further comprising a second printing step of forming, by screen printing prior to the firing step, a green second conductor layer which extends in a continuous manner on the second insulation sheet main surface of the green insulation portion as well as on the second electrolyte sheet main surface of the green electrolyte portion.

* * * * *